US009737214B2

(12) United States Patent
Proud

(10) Patent No.: US 9,737,214 B2
(45) Date of Patent: *Aug. 22, 2017

(54) WIRELESS MONITORING OF PATIENT EXERCISE AND LIFESTYLE

(71) Applicant: Hello Inc., San Francisco, CA (US)

(72) Inventor: James Proud, San Francisco, CA (US)

(73) Assignee: Hello Inc., San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/956,564

(22) Filed: Aug. 1, 2013

(65) Prior Publication Data

US 2014/0249393 A1   Sep. 4, 2014

Related U.S. Application Data

(63) Continuation-in-part of application No. 13/923,909, filed on Jun. 21, 2013, now Pat. No. 9,407,097, and
(Continued)

(51) Int. Cl.
*H04N 7/14* (2006.01)
*A61B 5/00* (2006.01)
(Continued)

(52) U.S. Cl.
CPC .......... *A61B 5/0024* (2013.01); *A61B 5/0022* (2013.01); *A61B 5/1118* (2013.01);
(Continued)

(58) Field of Classification Search
USPC ........................................................ 379/106
See application file for complete search history.

(56) References Cited

U.S. PATENT DOCUMENTS 3,127,363 A   3/1964   Nitzsche et al.
3,715,334 A   2/1973   Karstedt
(Continued)

FOREIGN PATENT DOCUMENTS

DE   3839900 A1   5/1990
EP   0183553 A2   6/1986
(Continued)

OTHER PUBLICATIONS

Davida, G.I., et al., "On enabling secure applications through off-line biometric identification", Proceedings of the IEEE Symposium on Security and Privacy (May 1998).
(Continued)

*Primary Examiner* — Maria El-Zoobi
(74) *Attorney, Agent, or Firm* — Paul Davis

(57) ABSTRACT

A system is provided that uses using telemetry data based on a patient habit information or patient monitoring. One or more patient monitoring devices has a unique patient ID, with personalized patient information. A patient monitoring device includes an application for monitoring exercise activity of a patient. ID circuitry is at the patient monitoring device, which includes ID storage and a communication system that reads and transmits the unique ID from an ID storage. A power source and a pathway system routes signals through the circuitry. A telemetry system is in communication with the patient monitoring device and includes a database of patient ID's which is in communication with the patient monitoring device and analyzes patient information based on the patient ID. The telemetry system receives exercise-related information directly or indirectly from the monitoring device that indicates an amount or type of exercise performed by the patient.

17 Claims, 24 Drawing Sheets

Related U.S. Application Data a continuation-in-part of application No. 13/923,637, filed on Jun. 21, 2013, now Pat. No. 8,810,430, and a continuation-in-part of application No. 13/923,614, filed on Jun. 21, 2013, now Pat. No. 8,850,421, and a continuation-in-part of application No. 13/923,809, filed on Jun. 21, 2013, now Pat. No. 9,425,627, and a continuation-in-part of application No. 13/923,750, filed on Jun. 21, 2013, now Pat. No. 9,438,044, and a continuation-in-part of application No. 13/923,583, filed on Jun. 21, 2013, now abandoned, and a continuation-in-part of application No. 13/923,560, filed on Jun. 21, 2013, now Pat. No. 8,803,366, and a continuation-in-part of application No. 13/923,543, filed on Jun. 21, 2013, and a continuation-in-part of application No. 13/923,937, filed on Jun. 21, 2013.

(60) Provisional application No. 61/772,265, filed on Mar. 4, 2013, provisional application No. 61/812,083, filed on Apr. 15, 2013, provisional application No. 61/823,502, filed on May 15, 2013.

(51) Int. Cl.
    *A61B 5/11*      (2006.01)
    *H02J 7/02*      (2016.01)
    *H02J 17/00*     (2006.01)
    *H02J 7/00*      (2006.01)
    *A61B 5/0205*    (2006.01)
    *H04L 29/08*     (2006.01)

(52) U.S. Cl.
    CPC ............ *H02J 7/025* (2013.01); *H02J 17/00* (2013.01); *A61B 5/02055* (2013.01); *A61B 5/6831* (2013.01); *A61B 2560/0214* (2013.01); *A61B 2562/08* (2013.01); *H02J 2007/0096* (2013.01); *H04L 67/12* (2013.01); *H04L 67/22* (2013.01)

(56) References Cited

U.S. PATENT DOCUMENTS

| | | |
|---|---|---|
| 3,775,452 A | 11/1973 | Karstedt |
| 3,813,364 A | 5/1974 | Zuba et al. |
| 3,814,730 A | 6/1974 | Karstedt |
| 4,394,317 A | 7/1983 | McAfee et al. |
| 4,603,152 A | 7/1986 | Laurin et al. |
| 4,780,556 A | 10/1988 | Hata et al. |
| 5,057,151 A | 10/1991 | Schuster et al. |
| 5,187,657 A | 2/1993 | Forbes |
| 5,319,363 A | 6/1994 | Welch et al. |
| 5,348,008 A | 9/1994 | Bornn et al. |
| 5,564,429 A | 10/1996 | Bornn et al. |
| 5,576,054 A | 11/1996 | Brown |
| 5,735,887 A | 4/1998 | Barreras, Sr. et al. |
| 5,910,544 A | 6/1999 | Ozawa et al. |
| 5,971,941 A | 10/1999 | Simons et al. |
| 6,038,315 A | 3/2000 | Strait et al. |
| 6,120,467 A | 9/2000 | Schallhorn |
| 6,200,289 B1 | 3/2001 | Hochman et al. |
| 6,221,012 B1 | 4/2001 | Maschke et al. |
| 6,323,846 B1 | 11/2001 | Westerman et al. |
| 6,416,471 B1 | 7/2002 | Kumar et al. |
| 6,440,067 B1 | 8/2002 | DeLuca et al. |
| 6,454,708 B1 | 9/2002 | Ferguson et al. |
| 6,570,557 B1 | 5/2003 | Westerman et al. |
| 6,580,356 B1 | 6/2003 | Alt et al. |
| 6,661,372 B1 | 12/2003 | Girerd et al. |
| 6,677,932 B1 | 1/2004 | Westerman |
| 6,893,396 B2 * | 5/2005 | Schulze ............... A61B 5/0022 600/300 |
| 7,113,932 B2 | 9/2006 | Tayebnejad et al. |
| 7,248,894 B2 | 7/2007 | Fujieda et al. |
| 7,502,643 B2 | 3/2009 | Farringdon et al. |
| 7,614,008 B2 | 11/2009 | Ording |
| 7,616,110 B2 | 11/2009 | Crump et al. |
| 7,633,076 B2 | 12/2009 | Huppi et al. |
| 7,653,883 B2 | 1/2010 | Hotelling et al. |
| 7,657,849 B2 | 2/2010 | Chaudhri et al. |
| 7,663,607 B2 | 2/2010 | Hotelling et al. |
| 7,720,855 B2 | 5/2010 | Brown |
| 7,733,224 B2 | 6/2010 | Tran |
| 7,844,914 B2 | 11/2010 | Andre et al. |
| 7,957,762 B2 | 6/2011 | Herz et al. |
| 7,959,567 B2 | 6/2011 | Stivoric et al. |
| 8,006,002 B2 | 8/2011 | Kalayjian et al. |
| 8,028,905 B2 | 10/2011 | Holberg |
| 8,033,996 B2 | 10/2011 | Behar |
| 8,044,363 B2 | 10/2011 | Ales et al. |
| 8,126,729 B2 | 2/2012 | Dicks et al. |
| 8,126,735 B2 | 2/2012 | Dicks et al. |
| 8,157,731 B2 | 4/2012 | Teller et al. |
| 8,204,786 B2 | 6/2012 | LeBoeuf et al. |
| 8,239,784 B2 | 8/2012 | Hotelling et al. |
| 8,251,903 B2 | 8/2012 | LeBoeuf et al. |
| 8,279,180 B2 | 10/2012 | Hotelling et al. |
| 8,328,718 B2 | 12/2012 | Tran |
| 8,352,211 B2 | 1/2013 | Vock et al. |
| 8,369,936 B2 | 2/2013 | Farringdon et al. |
| 8,378,811 B2 | 2/2013 | Crump et al. |
| 8,381,135 B2 | 2/2013 | Hotelling et al. |
| 8,389,627 B2 | 3/2013 | Rubinsztajn et al. |
| 8,390,463 B2 | 3/2013 | Munthe-Kaas et al. |
| 8,398,546 B2 | 3/2013 | Pacione et al. |
| 8,479,122 B2 | 7/2013 | Hotelling et al. |
| 8,587,426 B2 | 11/2013 | Bloem |
| 8,663,106 B2 | 3/2014 | Stivoric et al. |
| 2002/0015024 A1 | 2/2002 | Westerman et al. |
| 2002/0109600 A1 | 8/2002 | Mault et al. |
| 2002/0178126 A1 | 11/2002 | Beck et al. |
| 2003/0023467 A1 | 1/2003 | Moldovan |
| 2003/0121033 A1 | 6/2003 | Peev et al. |
| 2003/0143113 A2 | 7/2003 | Yuzhakov et al. |
| 2004/0044799 A1 | 3/2004 | Sivaraman et al. |
| 2004/0172290 A1 | 9/2004 | Leven |
| 2005/0113650 A1 | 5/2005 | Pacione et al. |
| 2005/0115561 A1 * | 6/2005 | Stahmann ............ A61B 5/0031 128/200.24 |
| 2005/0137480 A1 | 6/2005 | Alt et al. |
| 2005/0190059 A1 | 9/2005 | Wehrenberg |
| 2005/0245839 A1 | 11/2005 | Stivoric et al. |
| 2006/0017692 A1 | 1/2006 | Wehrenberg et al. |
| 2006/0026536 A1 | 2/2006 | Hotelling et al. |
| 2006/0030891 A1 | 2/2006 | Saltzstein et al. |
| 2006/0033724 A1 | 2/2006 | Chaudhri et al. |
| 2006/0064030 A1 | 3/2006 | Cosentino et al. |
| 2006/0066449 A1 | 3/2006 | Johnson |
| 2006/0089592 A1 | 4/2006 | Kadhiresan et al. |
| 2006/0098772 A1 | 5/2006 | Reho et al. |
| 2006/0136270 A1 | 6/2006 | Morgan et al. |
| 2006/0159645 A1 | 7/2006 | Miller et al. |
| 2006/0197753 A1 | 9/2006 | Hotelling |
| 2006/0264778 A1 | 11/2006 | Lim et al. |
| 2007/0021979 A1 * | 1/2007 | Cosentino ............ A61B 5/0031 705/2 |
| 2007/0033069 A1 * | 2/2007 | Rao ...................... A63B 24/00 705/2 |
| 2007/0149862 A1 | 6/2007 | Pipke |
| 2007/0167753 A1 | 7/2007 | Van Wyk et al. |
| 2007/0174633 A1 | 7/2007 | Draper et al. |
| 2008/0012701 A1 | 1/2008 | Kass et al. |
| 2008/0076969 A1 | 3/2008 | Kraft et al. |
| 2008/0146890 A1 | 6/2008 | LeBoeuf et al. |
| 2009/0023428 A1 | 1/2009 | Behzad et al. |
| 2009/0088820 A1 | 4/2009 | Mao et al. |
| 2009/0112247 A1 | 4/2009 | Freeman et al. |
| 2009/0119760 A1 | 5/2009 | Hung et al. |
| 2009/0182208 A1 | 7/2009 | Cho et al. |
| 2009/0234206 A1 | 9/2009 | Gaspard et al. |
| 2009/0240120 A1 | 9/2009 | Mensinger et al. |
| 2009/0255122 A1 | 10/2009 | Azrielant |

(56) References Cited

U.S. PATENT DOCUMENTS

| | | |
|---|---|---|
| 2009/0318773 A1 | 12/2009 | Jung et al. |
| 2010/0141042 A1 | 6/2010 | Kesler et al. |
| 2010/0153269 A1 | 6/2010 | McCabe |
| 2010/0234695 A1 | 9/2010 | Morris |
| 2010/0277003 A1 | 11/2010 | Von Novak et al. |
| 2011/0055132 A1 | 3/2011 | Mahdian et al. |
| 2011/0068935 A1 | 3/2011 | Riley et al. |
| 2011/0179450 A1 | 7/2011 | Kim et al. |
| 2012/0035487 A1 | 2/2012 | Werner et al. |
| 2012/0133079 A1 | 5/2012 | Sykes et al. |
| 2012/0146795 A1 | 6/2012 | Margon et al. |
| 2012/0149996 A1 | 6/2012 | Stivoric et al. |
| 2012/0170305 A1 | 7/2012 | Rudek et al. |
| 2012/0170521 A1 | 7/2012 | Vogedes et al. |
| 2012/0184876 A1 | 7/2012 | Freeman et al. |
| 2012/0194341 A1 | 8/2012 | Peichel et al. |
| 2012/0194419 A1 | 8/2012 | Osterhout et al. |
| 2012/0196832 A1 | 8/2012 | Luria |
| 2012/0205373 A1 | 8/2012 | Caldwell |
| 2012/0225719 A1 | 9/2012 | Nowozin et al. |
| 2012/0226639 A1 | 9/2012 | Burdick et al. |
| 2012/0229270 A1 | 9/2012 | Morley et al. |
| 2012/0242501 A1 | 9/2012 | Tran et al. |
| 2012/0253485 A1 | 10/2012 | Weast et al. |
| 2012/0253489 A1 | 10/2012 | Dugan et al. |
| 2012/0290327 A1 | 11/2012 | Hanlon et al. |
| 2012/0290950 A1 | 11/2012 | Rapaport et al. |
| 2012/0296455 A1* | 11/2012 | Ohnemus et al. ............... 700/91 |
| 2012/0302920 A1 | 11/2012 | Bridger et al. |
| 2012/0330109 A1 | 12/2012 | Tran |
| 2013/0022659 A1 | 1/2013 | Roberts |
| 2013/0030711 A1 | 1/2013 | Korhonen |
| 2013/0035785 A1 | 2/2013 | MacVittie et al. |
| 2013/0127980 A1 | 5/2013 | Haddick et al. |
| 2013/0154851 A1 | 6/2013 | Gaskill et al. |
| 2013/0172691 A1 | 7/2013 | Tran |
| 2013/0175732 A1 | 7/2013 | Lust et al. |
| 2013/0255681 A1 | 10/2013 | Batch et al. |
| 2013/0267794 A1 | 10/2013 | Fernstrom et al. |
| 2013/0326790 A1 | 12/2013 | Cauwels |
| 2014/0019468 A1 | 1/2014 | Federoff et al. |
| 2014/0129942 A1 | 5/2014 | Rathod |
| 2014/0236922 A1* | 8/2014 | Boyer .................. G06F 19/322 707/722 |
| 2014/0266939 A1 | 9/2014 | Baringer et al. |

FOREIGN PATENT DOCUMENTS

| | | |
|---|---|---|
| EP | 0271423 A1 | 6/1988 |
| EP | 0369255 A2 | 5/1990 |
| EP | 371004 A1 | 5/1990 |
| EP | 0477681 A2 | 4/1992 |
| EP | 0567253 A1 | 10/1993 |
| EP | 0640663 A2 | 3/1995 |
| EP | 0654497 A1 | 5/1995 |
| EP | 1094091 | 4/2001 |
| EP | 1094091 A1 | 4/2001 |
| EP | 1113042 A2 | 7/2001 |
| EP | 1133936 A1 | 9/2001 |
| EP | 1172414 A2 | 1/2002 |
| EP | 1217042 A1 | 6/2002 |
| EP | 1367534 A2 | 12/2003 |
| EP | 1371004 A2 | 12/2003 |
| EP | 1555297 A1 | 7/2005 |
| EP | 1595676 A1 | 11/2005 |
| EP | 1785454 A1 | 5/2007 |
| EP | 1792944 A1 | 6/2007 |
| EP | 1883798 A1 | 2/2008 |
| EP | 2052352 A1 | 4/2009 |
| EP | 2063555 A1 | 5/2009 |
| EP | 2428774 A1 | 3/2012 |
| EP | 2582116 A2 | 4/2013 |
| EP | 2614945 A2 | 7/2013 |
| GB | 1278798 A | 6/1972 |
| GB | 1381933 A | 1/1975 |
| GB | 2460890 A | 12/2009 |
| WO | WO-8704449 A1 | 7/1987 |
| WO | WO-9500992 A1 | 1/1995 |
| WO | WO-9956922 A1 | 11/1999 |
| WO | WO-02063555 A2 | 8/2002 |
| WO | WO-2006127726 A1 | 11/2006 |
| WO | WO-2008050951 A1 | 5/2008 |
| WO | WO-2012/170305 A1 | 12/2012 |
| WO | WO-2013076676 A1 | 5/2013 |
| WO | WO-2013081447 A1 | 6/2013 |

OTHER PUBLICATIONS

Juels, A., et al., "A Fuzzy Vault Scheme", Proceedings of the 2002 IEEE Symposium on Information Theory (Jun. 2002).

Juels, A., et al., "A fuzzy commitment scheme", Proc. 5th ACM Conference on Comp. and Commun. Security, pp. 28-36.

Yang, S., et al., "Secure fuzzy vault fingerprint verification system", Asilomar Conf. on Signals, Systems and Comp., vol. 1, pp. 577-581 (Nov. 2004).

Uludag, U., et al., "Fuzzy fingerprint vault", Proc. Workshop: Biometrics: Challenges arising from theory to practice, pp. 13-16 (Aug. 2004).

* cited by examiner

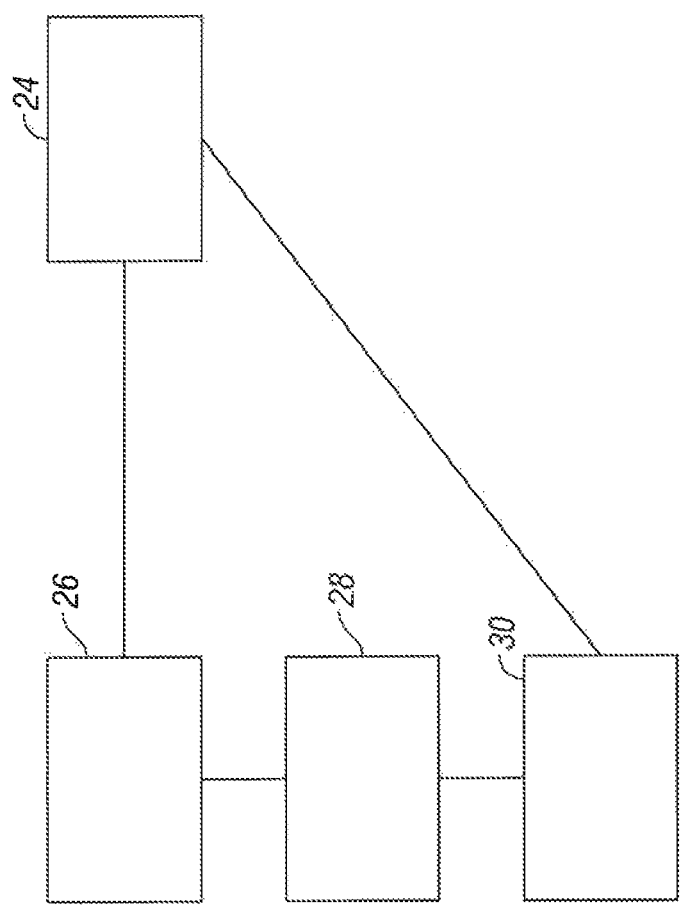

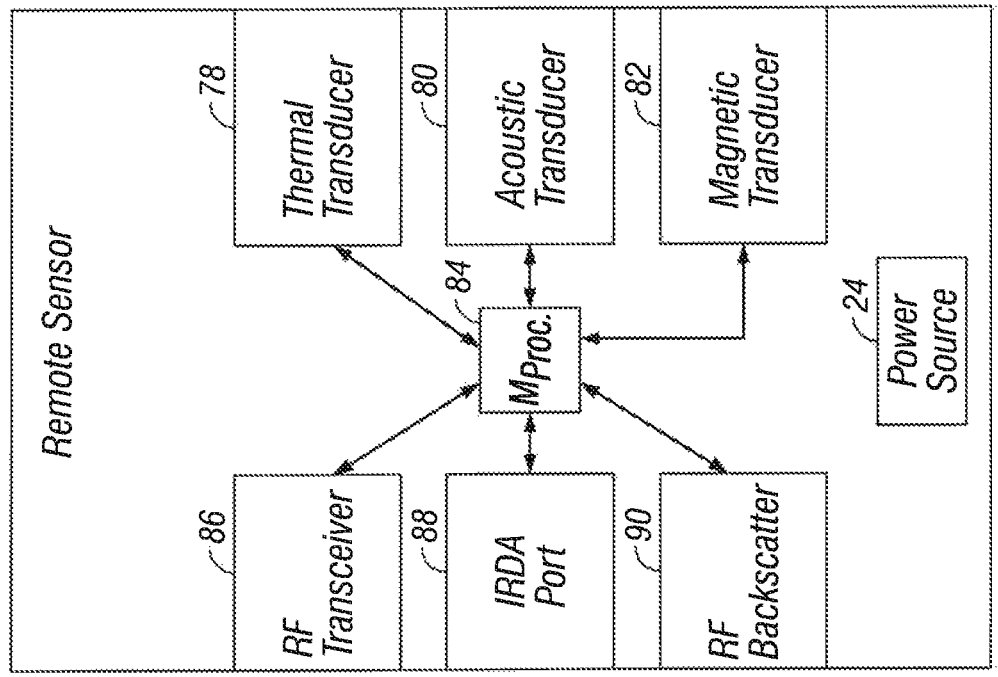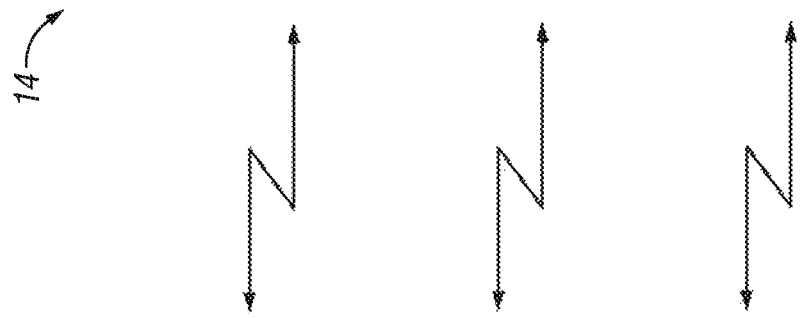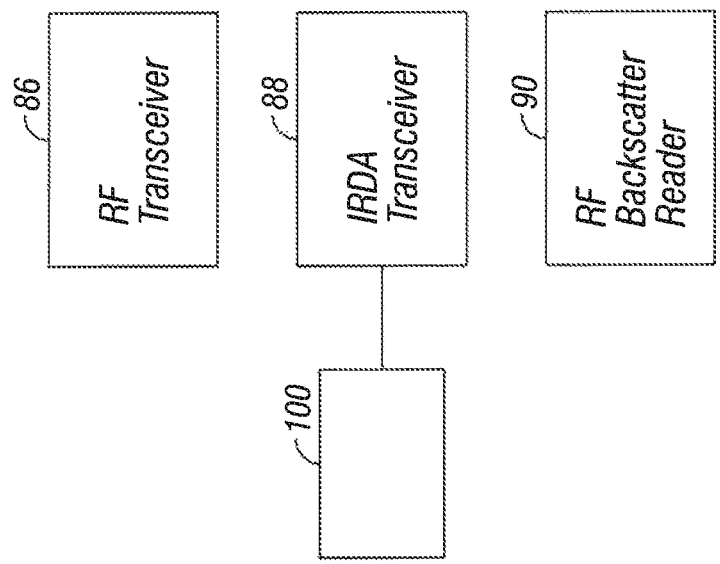
FIG. 10

WIRELESS MONITORING OF PATIENT EXERCISE AND LIFESTYLE

CROSS-REFERENCE TO RELATED APPLICATIONS

This application is a continuation in part of U.S. Ser. No. 13/923,909, U.S. Ser. No. 13/923,637, U.S. Ser. No. 13/923,614, U.S. Ser. No. 13/923,809, U.S. Ser. No. 13/923,750, U.S. Ser. No. 13/923,583, U.S. Ser. No. 13/923,560, U.S. Ser. No. 13/923,543, and U.S. Ser. No. 13/923,937, all filed Jun. 21, 2013 and all of which claim the benefit of U.S. 61/772,265, U.S. 61/812,083 and 61/823,502. All of the above-identified applications are fully incorporated herein by reference.

BACKGROUND

Field of the Invention

The present invention is directed to patient monitoring devices and telemetry systems, and more particularly to intelligent, patient monitoring devices with unique ID's for each patient that gather telemetry data based on patient's exercise activity and lifestyle.

Description of the Related Art

Patient monitoring was accomplished by electronic equipment maintained at the patient's bedside. Vital signs derived from physiological waveforms were monitored with the bedside equipment and alarms were generated if predetermined limits were exceeded by the vital signs. This bedside monitoring equipment became larger, more complex and expensive as each bedside unit undertook to monitor more physiological data and provide more sophisticated displays, e.g. color, more and better communications and more in-depth analysis of the data, such as calculation of vital signs and trends which required memory and processing capability. The provision of such units at each appropriate patient bedside introduces considerable additional expense to the hospital patient care costs.

With the introduction of bedside monitoring units, attempts were made to provide a measure of remote monitoring by transmitting analog waveforms of physiological data from the bedside unit to equipment at a central station such as a nurse's station. Subsequently remote monitoring efforts included analog waveforms plus digital representations for display. Both the bedside and remote monitoring activity acted to give alarms upon sensing an abnormal condition and to store data and analyze data to obtain vital signs and trends. But these systems are basically one-way systems reporting physiological data from the patient. There is no communication with the patient as a part of an interactive integrated system.

Telemetry systems can be implemented to acquire and transmit data from a remote source. Some telemetry systems provide information about a patient's activities.

It is becoming commonplace to use wireless packet data service networks for effectuating data sessions with. In some implementations, unique identifications (ID) need to be assigned to the devices in order to facilitate certain aspects of service provisioning, e.g., security, validation and authentication, et cetera. In such scenarios, it becomes imperative that no two devices have the same indicium (i.e., collision). Further, provisioning of such indicia should be flexible so as to maintain the entire pool of indicia to a manageable level while allowing for their widespread use in multiple service environments.

Medical telemetry systems may comprise an alarm adapted to identify high risk patients and/or patients requiring special assistance. Some medical procedures and diagnostic examinations require the removal of any telemetry system components attached directly to a patient. One problem with conventional medical telemetry systems is that the process of removing telemetry system components for purposes of performing a medical procedure or diagnostic examination can generate a false alarm. False alarms unnecessarily tax hospital resources and interfere with the working environment.

There is a need for telemetry devices configured to be used in patient monitoring. There is a further need for telemetry systems and patient monitoring devices for monitoring of patient's exercise activity and lifestyle.

SUMMARY OF THE INVENTION

An object of the present invention is to provide improved patient monitoring systems.

Another object of the present invention is to provide a system that includes a patient monitoring device that gathers telemetry data based on a patient's habits, patient condition or patient parameter in communication with a telemetry system, with analysis of the data to create personalized information about the patient's life.

A further object of the present invention is to provide systems that use a patient monitoring device or system that measures and tracks everything from a patient's movements and activities, to habits, lifestyle choices, health and social interactions.

Yet another object of the present invention is to provide telemetry systems in communication with a patient monitoring device that creates a unique portrait of a patient, and provides personalized information and mapping of a patient's daily experience.

Another object of the present invention is to provide telemetry systems and monitoring devices for monitoring a patient's lifestyle conditions, including diet, exercise and the like.

These and other objects of the present invention are achieved in a system for using telemetry data based on a patient habit information or patient monitoring. One or more patient monitoring devices has a unique patient ID. The one or more monitoring devices acquire patient information selected from of at least one of, a patient's activities, behaviors and habit information, and patient monitoring. A patient monitoring device includes an application for monitoring exercise activity of a patient. ID circuitry is at the patient monitoring device. The ID circuitry includes ID storage, a communication system that reads and transmits the unique ID from an ID storage. A power source and a pathway system routes signals through the circuitry. A telemetry system is in communication with the patient monitoring device. The telemetry system includes a database of patient ID's. The telemetry system is in communication with the patient monitoring device. The telemetry analyzes telemetry data based on at least one of, patient's activities, behaviors and habit information, patient condition and patient parameter. Personalized information is created about the patient. The telemetry system receives exercise-related information directly or indirectly from the monitoring device that indicates an amount or type of exercise performed by the patient.

In another embodiment of the present invention, a method is provided for remotely determining a type or amount of patient exercise. A patient monitoring device has a unique patient ID, an ID circuitry with ID storage, a communication system that reads and transmits the unique ID from an ID storage, a power source and a pathway system as well as a plurality of sensors. At least a portion of patient exercise or type of exercise information is received at the one or more sensors in response to at least one of a patient's activities, behaviors and habit information. Signals representative of patient exercise information are communicated directly or indirectly from the patient monitoring device to a remote telemetry system that includes a database of patient ID's, and a database of patient information. The telemetry system performs an analysis of an amount or type of exercise performed by the patient.

BRIEF DESCRIPTION OF THE DRAWINGS

FIG. 2 illustrates one embodiment of electronics that can be included in the wearable device.

FIG. 10 is a block diagram of a remote sensor shown in communication with two different external communication devices.

DETAILED DESCRIPTION

Figure 1A:
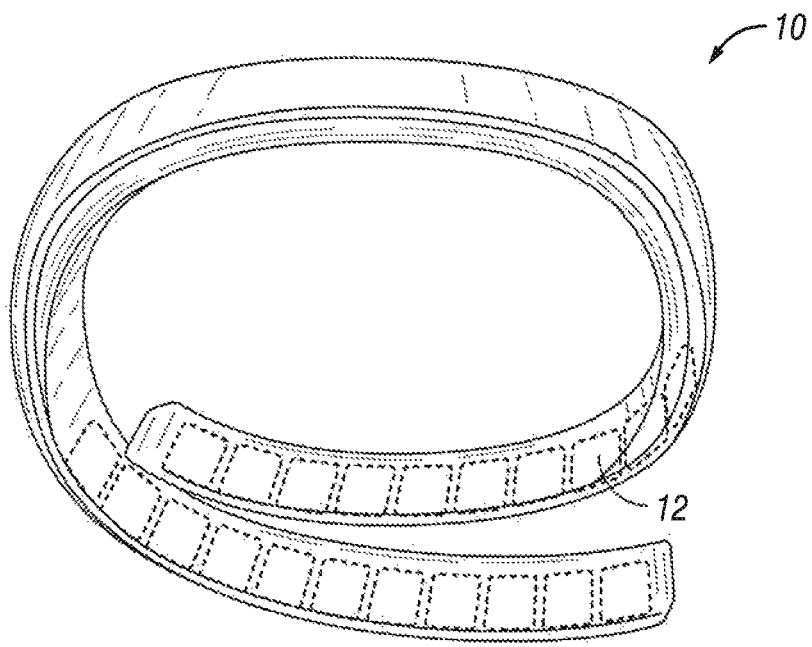
FIGS. 1(a) and 1(b) illustrate one embodiment of a wearable device of the present invention, where one size fits all.

As used herein, the term engine refers to software, firmware, hardware, or other component that can be used to effectuate a purpose. The engine will typically include software instructions that are stored in non-volatile memory (also referred to as secondary memory). When the software instructions are executed, at least a subset of the software instructions can be loaded into memory (also referred to as primary memory) by a processor. The processor then executes the software instructions in memory. The processor may be a shared processor, a dedicated processor, or a combination of shared or dedicated processors. A typical program will include calls to hardware components (such as I/O devices), which typically requires the execution of drivers. The drivers may or may not be considered part of the engine, but the distinction is not critical.

As used herein, the term database is used broadly to include any known or convenient means for storing data, whether centralized or distributed, relational or otherwise.

As used herein a mobile device includes, but is not limited to, a cell phone, such as Apple's iPhone®, other portable electronic devices, such as Apple's iPod Touches®, Apple's iPads®, and mobile devices based on Google's Android® operating system, and any other portable electronic device that includes software, firmware, hardware, or a combination thereof that is capable of at least receiving the signal, decoding if needed, exchanging information with a transaction server to verify the buyer and/or seller's account information, conducting the transaction, and generating a receipt. Typical components of mobile device may include but are not limited to persistent memories like flash ROM, random access memory like SRAM, a camera, a battery, LCD driver, a display, a cellular antenna, a speaker, a Bluetooth® circuit, and WIFI circuitry, where the persistent memory may contain programs, applications, and/or an operating system for the mobile device.

As used herein, the terms "social network" and "SNET" comprise a grouping or social structure of devices and/or individuals, as well as connections, links and interdependencies between such devices and/or individuals. Members or actors (including devices) within or affiliated with a SNET may be referred to herein as "nodes", "social devices", "SNET members", "SNET devices", "user devices" and/or "modules". In addition, the terms "SNET circle", "SNET group" and "SNET sub-circle" generally denote a social network that comprises social devices and, as contextually appropriate, human SNET members and personal area networks ("PANs").

A used herein, the term "wearable device" is anything that can be worn by an individual and that has a back side that in some embodiments contacts a user's skin and a face side.

Examples of wearable device include but are not limited to a cap, arm band, wristband, garment, and the like.

As used herein, the term "computer" is a general purpose device that can be programmed to carry out a finite set of arithmetic or logical operations. Since a sequence of operations can be readily changed, the computer can solve more than one kind of problem. A computer can include of at least one processing element, typically a central processing unit (CPU) and some form of memory. The processing element carries out arithmetic and logic operations, and a sequencing and control unit that can change the order of operations based on stored information. Peripheral devices allow information to be retrieved from an external source, and the result of operations saved and retrieved.

As used herein, the term "Internet" is a global system of interconnected computer networks that use the standard Internet protocol suite (TCP/IP) to serve billions of users worldwide. It is a network of networks that consists of millions of private, public, academic, business, and government networks, of local to global scope, that are linked by a broad array of electronic, wireless and optical networking technologies. The Internet carries an extensive range of information resources and services, such as the inter-linked hypertext documents of the World Wide Web (WWW) and the infrastructure to support email. The communications infrastructure of the Internet consists of its hardware components and a system of software layers that control various aspects of the architecture.

As used herein, the term "extranet" is a computer network that allows controlled access from the outside. An extranet can be an extension of an organization's intranet that is extended to users outside the organization that can be partners, vendors, and suppliers, in isolation from all other Internet users. An extranet can be an intranet mapped onto the public Internet or some other transmission system not accessible to the general public, but managed by more than one company's administrator(s). Examples of extranet-style networks include but are not limited to:
- LANs or WANs belonging to multiple organizations and interconnected and accessed using remote dial-up
- LANs or WANs belonging to multiple organizations and interconnected and accessed using dedicated lines
- Virtual private network (VPN) that is comprised of LANs or WANs belonging to multiple organizations, and that extends usage to remote users using special "tunneling" software that creates a secure, usually encrypted network connection over public lines, sometimes via an ISP As used herein, the term "Intranet" is a network that is owned by a single organization that controls its security policies and network management. Examples of intranets include but are not limited to:
- A LAN
- A Wide-area network (WAN) that is comprised of a LAN that extends usage to remote employees with dial-up access
- A WAN that is comprised of interconnected LANs using dedicated communication lines
- A Virtual private network (VPN) that is comprised of a LAN or WAN that extends usage to remote employees or networks using special "tunneling" software that creates a secure, usually encrypted connection over public lines, sometimes via an Internet Service Provider (ISP)

For purposes of the present invention, the Internet, extranets and intranets collectively are referred to as ("Network Systems").

As used herein, the term "patient" includes but not limited to a person, under a physician's care, interested in maintaining health, interested in maintaining a healthy lifestyle and/or physiologic balance, interested in monitoring lifestyle conditions, exercise, diet programs, and the like.

As used herein, the term (patient monitoring) includes: (i) Cardiac monitoring, which generally refers to continuous electrocardiography with assessment of the patient's condition relative to their cardiac rhythm. A small monitor worn by an ambulatory patient for this purpose is known as a Holter monitor. Cardiac monitoring can also involve cardiac output monitoring via an invasive Swan-Ganz catheter (ii) Hemodynamic monitoring, which monitors the blood pressure and blood flow within the circulatory system. Blood pressure can be measured either invasively through an inserted blood pressure transducer assembly, or noninvasively with an inflatable blood pressure cuff. (iii) Respiratory monitoring, such as: pulse oximetry which involves measurement of the saturated percentage of oxygen in the blood, referred to as SpO2, and measured by an infrared finger cuff, capnography, which involves CO2 measurements, referred to as EtCO2 or end-tidal carbon dioxide concentration. The respiratory rate monitored as such is called AWRR or airway respiratory rate). (iv) Respiratory rate monitoring through a thoracic transducer belt, an ECG channel or via capnography, (v) Neurological monitoring, such as of intracranial pressure. Special patient monitors can incorporate the monitoring of brain waves electroencephalography, gas anesthetic concentrations, bispectral index (BIS), and the like, (vi) Blood glucose monitoring using glucose sensors. (vii) Childbirth monitoring with sensors that monitor various aspects of childbirth. (viii) Body temperature monitoring which in one embodiment is through an adhesive pad containing a thermoelectric transducer. (ix) Stress monitoring that can utilize sensors to provide warnings when stress levels signs are rising before a human can notice it and provide alerts and suggestions. (x) Epilepsy monitoring. (xi) Toxicity monitoring, and the like.

Additionally the present invention can be used to detect differences for a variety of blood tests, including but not limited to tests for the following: sodium, potassium, chloride, urea, creatinine, calcium, albumin, fasting glucose, amylase, carcinoembryonic antigen, glycosylated hemoglobin, hemoglobin, erthrocytes hemoglobin and the like.

Figure 1B:
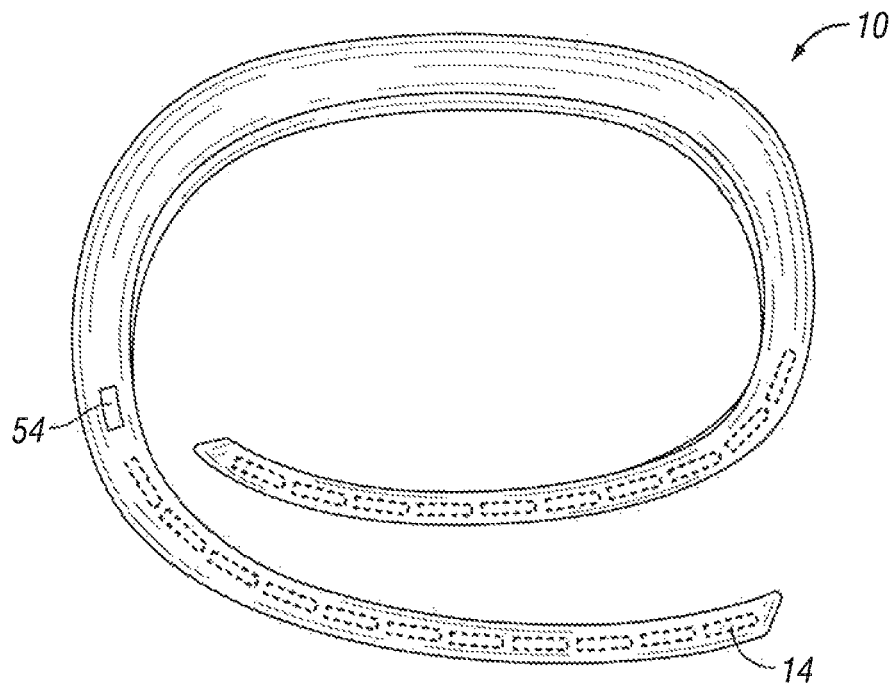

In various embodiments, the present invention provides a patient monitoring device 10, such as a wearable device, where one size fits all. As illustrated in FIGS. 1(a) and 1(b), in one embodiment of the present invention, the patient monitoring device 10 include a plurality of magnets 12, with adjacent magnets having opposite polarity, with a length suitable to be worn by all people. In one embodiment, the length of the patient monitoring device 10 can be 10-12 inches. The magnets 12 are positioned along an interior of the patient monitoring device 10 to be provided for good conformation to a user's wrist.

One or more sensors 14 are coupled to the patient monitoring device 10. The sensors are measuring devices. As a non-limiting example, the measuring device or sensors 14 can include RTSS devices to detect a user's activities, motions, physical parameters, and the like, including but not limited to, a heart rate monitor, a body temperature probe, a conventional pedometer, an accelerometer and the like.

Alternatively, multifunctional sensors 14 which can perform all the aforementioned functions of RTSS may be attached or embedded in patient monitoring device 10. In one embodiment, each sensor can be in communication and or connect electronically and/or RF to a telemetry module 16. A variety of different sensors 14 can be utilized, including but not limited to, an accelerometer based sensor, and pressure based sensors, voltage resistance sensor, a radio frequency sensor, and the like, as recited above.

As a non-limiting example, an accelerometer, well known to those skilled in the art, detects acceleration and thus user activity. The accelerometer provides a voltage output that is proportional to the detected acceleration. Accordingly, the accelerometer senses vibration. This voltage output provides an acceleration spectrum over time; and information about loft time can be ascertained by performing calculations on that spectrum. A microprocessor subsystem, such as disclosed in U.S. Pat. No. 8,352,211, incorporated herein by reference, stores the spectrum into memory and processes the spectrum information to determine activity. Other examples of suitable accelerometer sensors are disclosed in EP 2428774 A1, incorporated herein by reference. Suitable pressure sensors are disclosed in EP 1883798 B1, incorporated herein by reference. A suitable voltage resistance sensor is disclosed in EP 1883798 B1, incorporated herein by reference. A suitable radio frequency sensor is disclosed in EP 2052352 B1, incorporated herein by reference.

Referring to FIG. 2, in various embodiments, the patient monitoring device 10, also known as the patient monitoring device, can include a power source 24, such a battery that can be rechargeable. The battery 24 can be put into a sleep state when not actively used in order to preserve power. A wake up feature allows the battery 24 and other electronics of the patient monitoring device 10 to "sleep" during non-use or and is initiated into the "wake up" mode by certain predestinated events.

Figure 3:
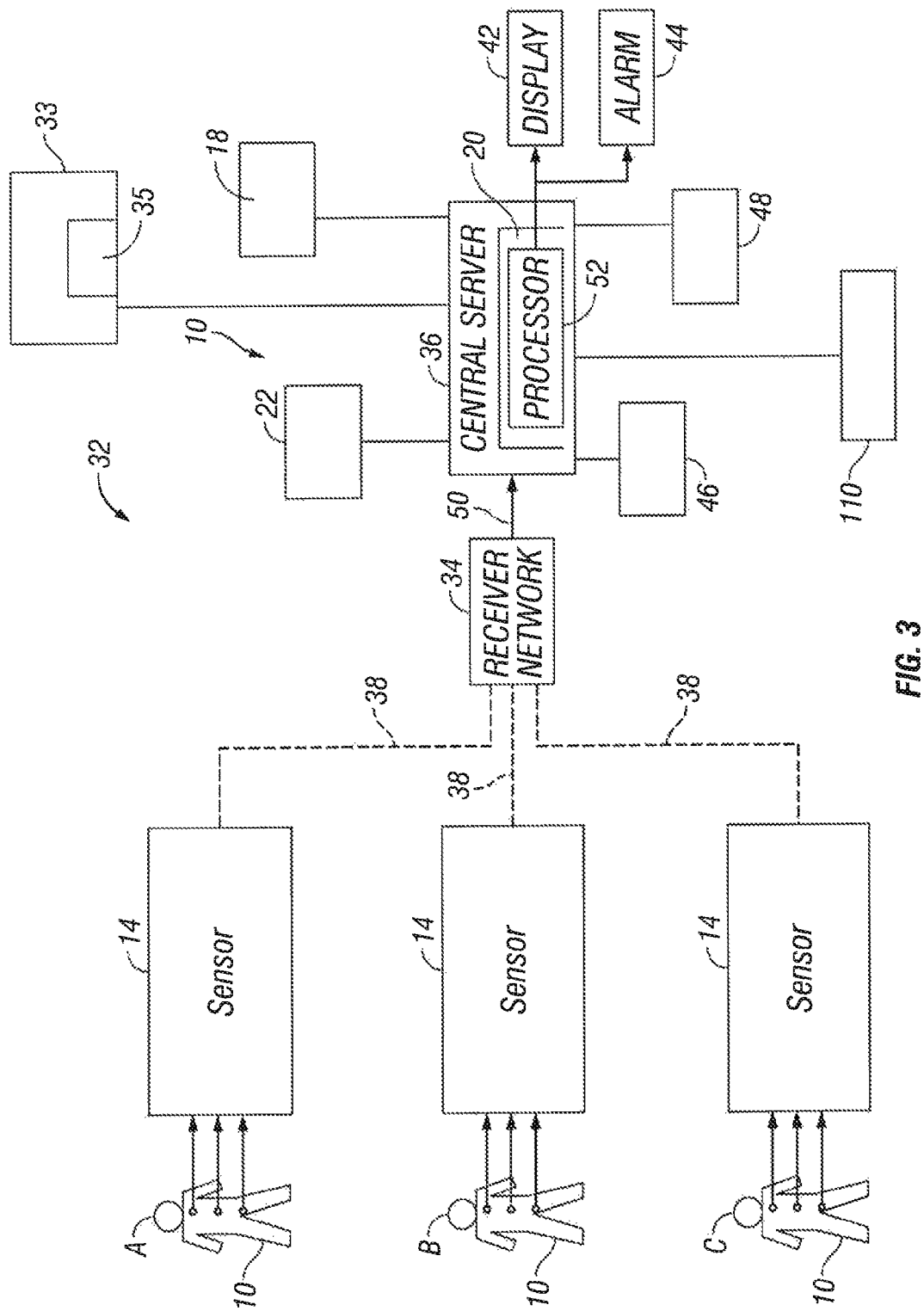
FIG. 3 illustrates one embodiment of a telemetry system of the present invention.

In one embodiment, as illustrated in FIG. 3, a telemetry system server 16 is coupled to a database 18. Each patient monitoring device 10 is assigned its own unique identification, ID.

The data transmitted by the patient monitoring device 10 sensors 14 and its ID may be coded by appending a seed to digital data bits. As illustrated in FIG. 3 central processor unit 20 (CPU) validates or rejects received upon detection of the seed string appended to the digital data bits. In the alternative, the digital data bits may be coded and decoded by applying a scrambling algorithm utilizing the seed. A programming device 22 may be configured to transmit data to a sensor 14, also known as a patient monitoring device, utilizing a variety of alternative transmission means, including, for example, RF, IR, optical, and the like, or a magnetic loop/induction system.

In one embodiment, sensors 14 are configured to be shipped to users in a non-programmable mode with all programming already performed at the factory. A random seed may be communicated to the programming device 22 can a variety of different mechanisms, including but not limited to, via scanning a bar code, manual input, magnetic strip, random number generation, and the like.

Referring again to FIG. 2, in one embodiment, the patient monitoring device 10 includes a control unit 26 that puts the patient monitoring device 10 in a low power state. A monitoring system 28 can be included that remains active. The monitoring system 28 wakes up the electronics 30 in the patient monitoring device 10 from a low power state. The control unit 26 can be notified of awaking of the other components by the monitoring system 28. The control unit 26 can set a status bit on the monitoring system 28 only when the battery 24 needs to be in a full power state. The control unit 26 then forces a power cycle.

Referring to FIG. 3, one embodiment of a telemetry system 32 is illustrated. The telemetry system 32 is in the communication with the sensors 14 and or patient monitoring device 14 and ID of the patient monitoring device 10 and can include one or more receivers 34, a central server 36 with the CPU 20. The telemetry system 32 can optionally include a display 42 and an alarm 44. The telemetry system 32 receives information from sensors 14 and or the monitoring device of a user's habits, activities, and the like, and then processes this information. Patient monitoring device 10 with its unique ID and sensors 14 is assigned to a specific user in order to track and/or monitor that user. For illustrative purposes assume that three users A, B AND C are being tracked and monitored by the telemetry system 32. It should, however, be appreciated that the telemetry system 32 may be implemented to track and/or monitor a much larger number of users.

In one embodiment of the present invention, radio frequency (RF) devices that are sensors 14 and/or chips may serve as the identifying devices. Each source, sensor 14, ID and the like can carry a fixed radio frequency chip encoded with identifying data which may be correlated to the individual participants, parts or objects.

Telemetry system 32 of the present invention may include a Real-Time Location System (RTLS) 46 and Real-Time Sensing System (RTSS) 48 with RF technology. The RF technology may include active and/or passive RFID sensors 14 and an RF wireless array system as a receiver 34. The RF technology in the RTLS 46 and RTSS 48 may include UWB technology (e.g., IEEE 802.15), WLAN technology (e.g., IEEE 802.11), SAW RFID positioning system technology, GPS technology, and the like.

The sensors 14 may communicate directly with each other and/or relay telemetry data directly to base receiving RF device(s) or base receivers 34. The base receivers 34 may forward the telemetry data to a base computer either through a direct link or through a network. Alternatively the telemetry data may be forwarded to end user devices, including but not limited to, laptops, mobile devices and the like, either directly or through a network. The comprehensive telemetry system 32 using RF technologies such as UWB, ZigBee, Wi-Fi, GPS data system can be utilized as described above.

The readers/antennae may be interconnected using a LAN, such as Ethernet to provide a network communication infrastructure for the computers and servers. Active and passive RFID sensors 14 may be employed. The active sensors 14 (RFID) may have a two-way communication function, which allows the base computer system to dynamically manage the sensors 14; vary update rates; send self-identification and telemetry data.

The active sensors 14 may employ dual-radio architecture. In one embodiment, active sensors 14 transmit radio pulses, which are used to determine precise two-dimensional or three-dimensional location and a conventional bi-directional radio, which is used as a control and telemetry channel with a sensor update rate.

The patient monitoring device 10 gathers telemetry data, communicates that data to a base station, BLUETOOTH® enabled device, or smart phone and the like. From the base station, the patient monitoring device 10 can receive firmware updates or via a BLUETOOTH® enabled device. The patient monitoring device 10 can receive updates wirelessly. The base station can receive firmware updates from Network Systems, take telemetry data from the patient monitoring device 10 and transfer it to Network Systems. Telemetry data received from the base station is analyzed by servers and presented to an end user. Any third party device can receive data from the patient monitoring device 10 wirelessly and deliver information to the servers for processing.

In one embodiment, the patient monitoring device 10 uses an accelerometer, gyroscope, GPS sensor, a BLUETOOTH® chip, and a heart rate monitor.

As a non-limiting example, for heart monitoring, the accelerometer, sensor 14, determines when to sample the sensors 14 and to improve the accuracy of the heart rate monitor. The gyroscope detects movement and orientation and the GPS sensor is used to determine location of the user. A BLUETOOTH® chip allows the device to connect wirelessly to other third party devices.

As a non-limiting example, a heart rate monitor 14 detects the user's heart rate in order to accurately determine the user's activity level, behavioral patterns and the like.

An Artificial Intelligence (AI) or Machine Learning-grade algorithms is used to identify the user's activities, behaviors, behaviors and perform analysis. Examples of AI algorithms include Classifiers, Expert systems, case based reasoning, Bayesian networks, and Behavior based AI, Neural networks, Fuzzy systems, Evolutionary computation, and hybrid intelligent systems. A brief description of these algorithms is provided in Wikipedia and stated below.

Classifiers are functions that can be tuned according to examples. A wide range of classifiers are available, each with its strengths and weaknesses. The most widely used classifiers are neural networks, support vector machines, k-nearest neighbor algorithms, Gaussian mixture models, naive Bayes classifiers, and decision trees. Expert systems apply reasoning capabilities to reach a conclusion. An expert system can process large amounts of known information and provide conclusions based on them.

A case-based reasoning system stores a set of problems and answers in an organized data structure called cases. A case based reasoning system upon being presented with a problem finds a case in its knowledge base that is most closely related to the new problem and presents its solutions as an output with suitable modifications. A behavior based AI is a modular method of building AI systems by hand. Neural networks are trainable systems with very strong pattern recognition capabilities.

Fuzzy systems provide techniques for reasoning under uncertainty and have been widely used in modern industrial and consumer product control systems. An Evolutionary Computation applies biologically inspired concepts such as populations, mutation and survival of the fittest to generate increasingly better solutions to the problem. These methods most notably divide into evolutionary algorithms (e.g., genetic algorithms) and swarm intelligence (e.g., ant algorithms). Hybrid intelligent systems are any combinations of the above. It is understood that any other algorithm, AI or otherwise, may also be used. Examples of suitable algorithms that can be used with the embodiments of the present invention are disclosed in, EP 1371004 A4, EP 1367534 A2, US 20120226639 and US 20120225719, all incorporated fully herein by reference.

In various embodiments, the patient monitoring device 10 has additional features. In one embodiment, the patient monitoring device 10 changes color, via infrared LEDs, to accurately match the wearer's skin tone. This creates a seamless and more personal integration of technology into the user's daily life. In this embodiment, there is skin contact with the patient monitoring device 10.

In another embodiment, the patient monitoring device 10 remotely reminds and can be used to administer medications. As a non-limiting example, the patient monitoring device 10 can inject adrenalin. In one embodiment, the patient monitoring device 10 has sleep pattern recognition based on movement and heart rate.

In various embodiments, the patient monitoring device 10 uses algorithms to determine activity type, behavioral patterns and user habits based on collected data.

In one embodiment, the patient monitoring device 10 uses the accelerometer information to improve the heart rate monitor. As a non-limiting example, the patient monitoring device 10 detects movement and speed. Addition of this data improves the accuracy of the heart rate monitor and corrects for any miscalculations in vibration, noise and skin color.

In one embodiment, velocity readouts and accelerometer data are used to measure when to sample heart rate. For example, if the patient monitoring device 10 registers zero velocity readout, the user is probably at rest or engaged in a passive activity. Thus, the patient monitoring device 10 knows not to sample heart rate. This results in conversation of time, energy and data storage.

User activity, performance and action can be based on the acceleration and angular velocity of the patient monitoring device 10. In one embodiment, the patient monitoring device 10 has a feature where the patient monitoring device 10 authorizes third party interaction based on hand gesture, on previous interactions or patterns of behavior. As a non-limiting example, if one purchases a coke every day for the last two weeks, the patient monitoring device 10 can "orders" the person another one based on the prior history.

In one embodiment, the patient monitoring device 10 features near-by patient monitoring device 10 recognition that provides for other patient monitoring device 10 devices to be recognized within a particular vicinity and are able to share and transfer data between them. The patient monitoring device 10's data analysis and feedback can be based on current or previous sensor output. The patient monitoring device 10 can alert the user when to charge the patient monitoring device 10 and when it is the most convenient for the user.

In one embodiment, the patient monitoring device 10 provides feedback via color change. An outer shell of the patient monitoring device 10 can use visual feedback, including but not limited to pigment or color changes to indicate changes in user behavior or to prompt changes in user behavior. In one embodiment, the patient monitoring device 10 is flexible in shape. As a non-limiting example, if the user puts the patient monitoring device 10 over their hand it can expand or contract, morphing to change size and shape.

In one embodiment, the patient monitoring device 10 can have a sync feature for multiple bands at the same time.

In one embodiment, the patient monitoring device 10 has data transfer to an external device that can be included or not included in system 32. Patient monitoring device 10 could be a data leaching device. For example, the user can relay information to someone else's device (intermediary device) to access Network Systems connected device.

In one embodiment, the patient monitoring device 10 can disable the recording of one or more sensors 14 based on location, acceleration (or lack thereof) and the like.

In one embodiment, the patient monitoring device 10 detects different types of transportation and activity based on sensor data. In one embodiment, patient monitoring device 10 can unlock doors or cars. The user can turn it on and off. As a non-limiting example, it can be turned off by having a capacitor switch on top and bottom and is placed in a way that one couldn't accidentally turn it off. As a non-limiting example, turning it off can be done by rotating the patient monitoring device 10 once.

In one embodiment, the patient monitoring device 10 recognizes the wearer based on biometric information, previous data, movement pattern, and the like. In one embodiment, the patient monitoring device 10 detects a new user based on an inability to match to user/usage patterns.

As non-limiting examples, a variety of different sensors 14 can be used such as, an altimeter, blood oxygen recognition, heart rate from wrist via sonar, Doppler, based on sound wave and movement, based on pressure, and the like. A pressure sensor 14 can be placed on a circulatory vessel such as a vein to detect pulse.

With the patient monitoring device 10 of the present invention, mechanical actions of the user can be triggered, recognized and evaluated.

As a non-limiting example, with multiple users and wearable devices 10, a separate patient monitoring device 10 ID is assigned to each of the users A, B AND C, and thereafter the assigned transmitter/monitor 14 generates user activity data and/or user tracking data. For purposes of this disclosure, monitoring data is defined to include data acquired during the process of monitoring or evaluating a predefined characteristic. The user activity data tracks data from the sensors 14 is transferred to the receivers 34 via the wireless connections 38 represented by a dashed line.

A network of receivers 34 transfers the user activity and/or tracking data to system server 16 via connection 50. System server 16 includes a processor 52 configured to process the user data in a known manner. For example, the processor 52 may convert raw user data acquired by the sensors 14 into more conveniently readable data.

As a non-limiting example, the display 42 can be implemented to graphically convey user information from system server 16 in a conveniently readable manner. As a non-limiting example, the user may be a cardiac patient with user monitoring data graphically conveyed as a conventional ECG plot comprising a sequence of P-waves, a QRS complexes and a T-waves. As another example, user tracking data may be graphically conveyed as an icon superimposed onto a map to indicate the user's relative location. Alarm 44 may be included in this embodiment.

In some embodiments, system 32 ID circuitry delivers a unique ID to the wearable device from database 18. Bluetooth chips can be coupled with other wearable devices 10 in the area. This data is then stored, as more fully explained in the following paragraph. The unique ID can be utilized for a variety of different applications including but not limited to payments, social networking and the like.

The ID circuitry of system 32 can include a number of system/components: unique ID storage, communication system, which reads and transmits the unique ID from the unique ID storage, battery 24 or power system that provides power to enable communication with the patient monitoring device 10, a pathway system to route signals to through the circuitry, a cluster that crunches information, and a control system, to orchestrate the communication between different systems. All of these systems can be implemented in hardware, software or a combination thereof. Continuing with the telemetry system 32, sensors 14 and sensing devices are disposed on wearable devices 10 worn by users. Data, such as movement, location, speed, acceleration, and the like, can be acquired, captured and provided to system 32.

System 32 and an associated network can include an identification reference, including user activity, performance and reference information for each individual sensor 14 and location.

The user activity, performance metrics, data and the like captured by system 32 can be recorded into standard relational databases SQL server, and/or other formats and can be exported in real-time.

In various embodiments, the patient monitoring device 10 and/or system 32 are fully sealed and have inductively charges. All communication is done wirelessly.

In one embodiment, there are no electrical contacts, physical contacts or connections with the patient monitoring device 10. The patient monitoring device 10 is seamless. The telemetry system 32 can include a microprocessor with CPU 20, memory, interface electronics and conditioning electronics 33 configured to receive a signal from the sensors 14. In one embodiment, all or a portion of the conditioning electronics 33 are at the patient monitoring device 10.

In one embodiment, the CPU 20 includes a processor 52, which can be a microprocessor, read only memory used to store instructions that the processor may fetch in executing its program, a random access memory (RAM) used by the processor 52 to store information and a master dock. The microprocessor is controlled by the master clock that provides a master timing signal used to sequence the microprocessor 52 through its internal states in its execution of each processed instruction. In one embodiment, the microprocessor 52, and especially the CPU 20, is a low power device, such as CMOS, as is the necessary logic used to implement the processor design. The telemetry system 32 can store information about the user's activity in memory.

This memory may be external to the CPU 20 but can reside in the RAM. The memory may be nonvolatile such as battery backed RAM or electrically erasable programmable read only memory (EEPROM). Signals from the sensors 14 can be in communication with conditioning electronics 33 that with a filter 35, with scale and can determine the presence of certain conditions. This conditioning essentially cleans the signal up for processing by CPU 20 and in some cases preprocesses the information. These signals are then passed to interface electronics, which converts the analog voltage or currents to binary ones and zeroes understood by the CPU 20. The telemetry system 32 can also provide for intelligence in the signal processing, such as achieved by the CPU 20 in evaluating historical data.

In one embodiment, the actions of the user wearing the patient monitoring device 10 with the unique ID can be used for different activities and can have different classifications at system 32.

The classification can be in response to the user's location, where the user spends it time, with which the user spends its time, determination of working relationships, family relationships, social relationships, and the like. These last few determinations can be based on the time of day, the types of interactions, comparisons of the amount of time with others, the time of day, a frequency of contact with others, the type of contact with others, the location and type of place where the user is at, and the like. These results are stored in database 18.

In one embodiment, the user wearing the patient monitoring device 10 can access this information from any place where data is presented to the user, including but not limited to mobile devices, the WEB, applications program identifiers, and the like.

As a non-limiting example, the patient monitoring device 10 communicates with a base station at system 32. The patient monitoring device 10 can intelligently switch between data transfer and charging based on sensor readout. The patient monitoring device 10 can represent data based on connected devices.

In one embodiment, the patient monitoring device 10 has the capability of providing recommendations, popularity of locations or activities based on acquired data from the user.

In one embodiment, the patient monitoring device 10 has the capability of introducing the user to other people or users based on their data and the user's data.

In one embodiment, the patient monitoring device 10 can determine emotion of the user.

In one embodiment, the patient monitoring device 10 uses incremental data transfer via BLUETOOTH® and the like. The patient monitoring device 10 can transmit data through the inductive coupling for wireless charging. The user is also able to change the frequency of data transmission.

The patient monitoring device 10 can engage in intelligent switching between incremental and full syncing of data based on available communication routes. As a non-limiting example, this can be via cellular networks, WiFi, BLUETOOTH® and the like. In one embodiment, the patient monitoring device 10 has data storage. As a non-limiting example, storage of telemetry data on patient monitoring device 10 can be amounts up to about 16 mg.

In one embodiment, data transferred if it's in a selected proximity of a base station of system 32 or in proximity of an associated connected network. In one embodiment, the patient monitoring device 10 has a dynamic change of data capture frequency. The patient monitoring device 10 can be programmed to instantly change how often it samples any sensor 14 based upon the sensor data. Intelligent data sampling is based on sensor readout.

The patient monitoring device 10 can receive firmware updates via a base station 110 of system 32. In one embodiment, the patient monitoring device 10 presents analyzed data and feedback on a website. In one embodiment, the patient monitoring device 10's software is based on unique human movement. The patient monitoring device 10 is able to identify its wearer based on the unique patterns of movement, location check-ins and daily habits of the user.

In one embodiment, the app can be used on a mobile device, including but not limited to a smart phone and the like.

In one embodiment, a breakdown of recounting data that has been collecting is presented for analysis of that data. Observation or recommendations can be presented based on historical information and live information. The importance of the data can be based on past user behavior.

In one embodiment, the patient monitoring device 10 has artificial intelligence. A wearable device processor 54 implements logic resources that exist on patient monitoring device 10.

In one embodiment, patient monitoring device 10 engages in the routing of user information to third parties based on predefined rules, based on system 32 analysis.

In one embodiment, patient monitoring device 10 includes one or more processors 54 that implement intelligent algorithmic processing and transfer of information to third parties. Feedback can be provided to the end user that is based on visual, tactile, gesture information and the like.

Figure 4:
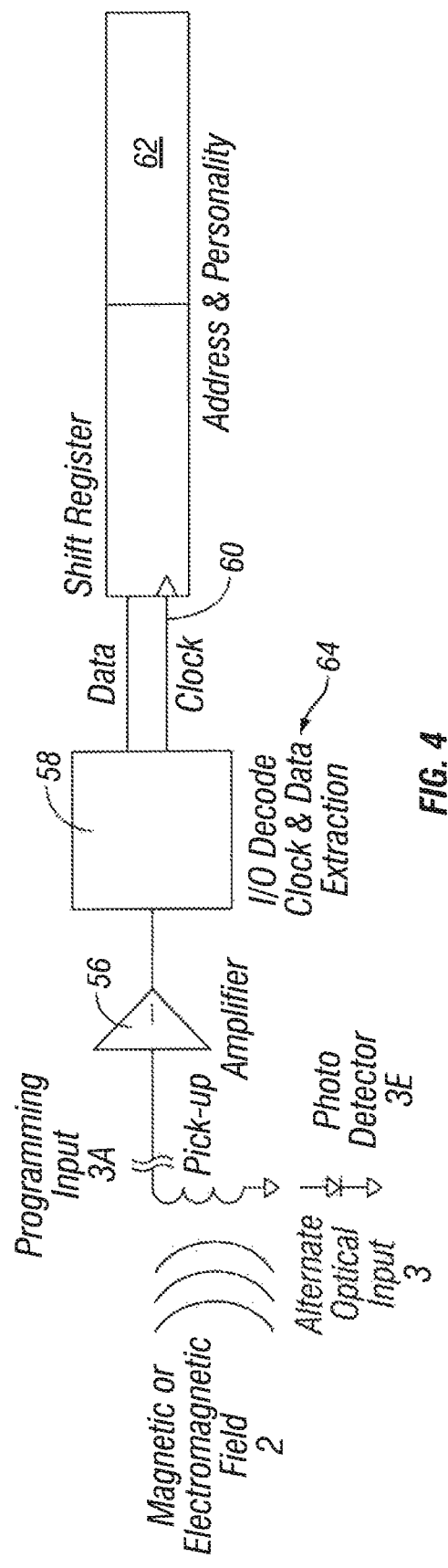
FIG. 4 is a diagram of the programming input schematic of the secure sensor/transmitter array of FIG. 7.

The ID can be sent from the patient monitoring device 10 in a variety of different transmit modes, which may be provided as part of the firmware or software of an ID or sensor transmitter 14, and which may be utilized selectively during the operation of said sensor transmitter 14, may include 'burst' transmit modes, wherein a burst of data information is transmitted, or "parcel" transmit modes, wherein timed data packets of data, which may, as desired, comprise partial data strings, are transmitted, and, if desired, repeated during time intervals. Further, the sensors 14 may have programmed therein diagnostic routines or other test modes which assist during manufacture and use, providing the operator with operational status and verification information on said sensor/transmitter 14, as needed. Referring to FIG. 4, system 32 includes data base 18 which contains the desired transmitter, sensor, 14 personality data, as well as, the address/device ID bits for each patient monitoring device 10.

In one embodiment, the initial programming of the patient monitoring device 10 for the ID, as well as optionally other personal information of the user, is done securely, as unauthorized future alteration of same thereafter can be utilized as a means of violating system integrity.

In one embodiment, an inductive field coil is used for programming the sensors 14 and ID of patient monitoring device 10.

As illustrated in FIG. 4, the patient monitoring device 10 can include a sensor 14 with an output that be received by an amplifier 56 and decoded by an I/O decoder 58 to determine I/O logic levels, as well as, both clock and data information 60. Many such methods are commonly available including ratio encoding, Manchester encoding, Non-Return to Zero (NRZ) encoding, or the like; alternatively, a UART type approach can be used. Once so converted, clock and data signals containing the information bits are passed to a memory 62. Any of these connections provides a logical link from the system's database 18 to the sensor 14, ID of the patient monitoring device 10, as shown in FIG. 5.

Figure 5:
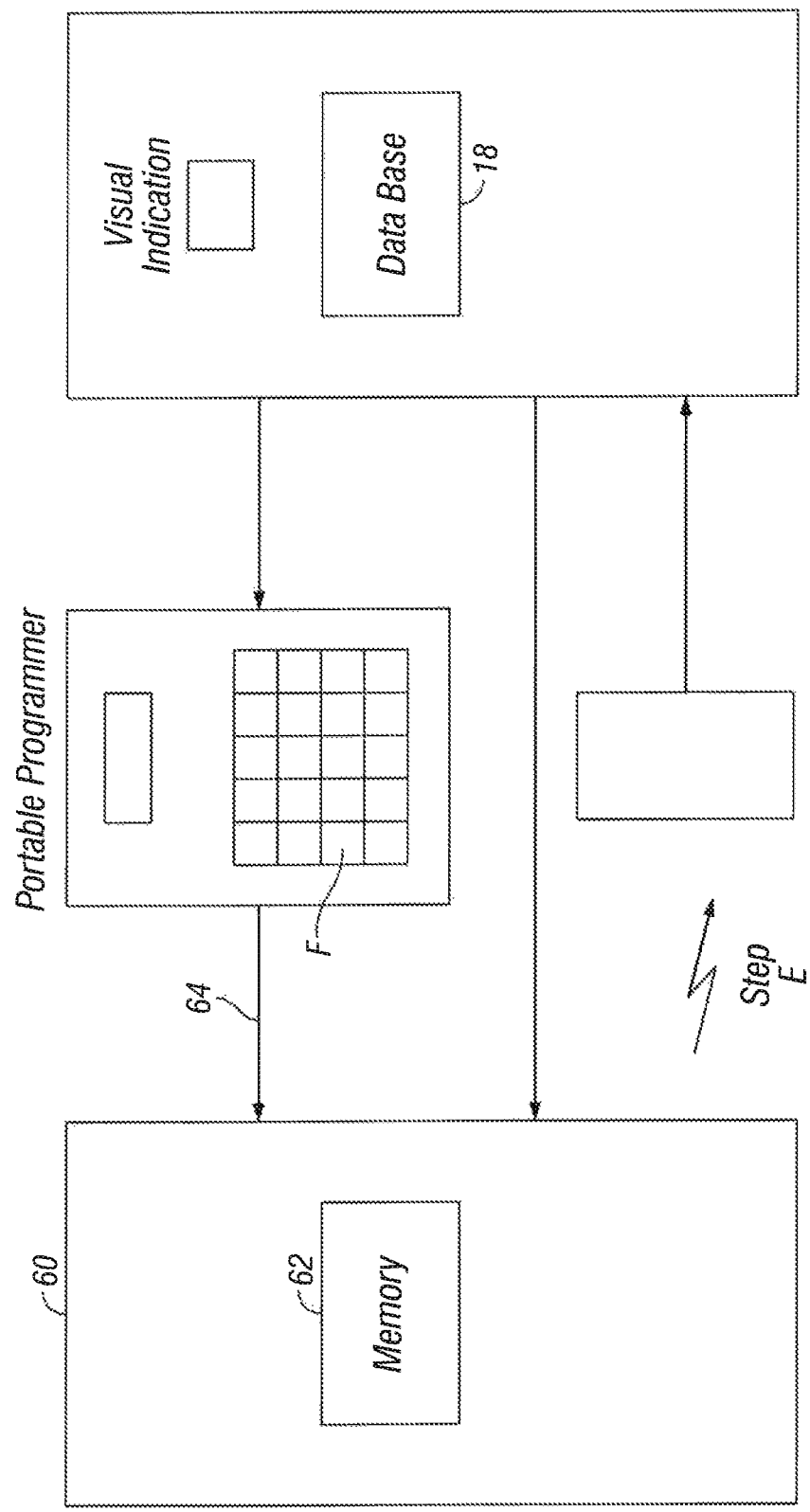
FIG. 5 is a block diagram of the system of programming the sensor/transmitter(s) comprising the secure sensor/transmitter array of FIG. 7.

In one embodiment, illustrated in FIG. 5, the system 32 chooses the necessary programmable sensor functions and stores them into database 18. In one embodiment, in order to insure that an unauthorized user cannot connect into and program patient monitoring device 10 the following procedure may be used:

Both the sensor 14 and receiver 34 contain an identical, repeatable pseudo randomization algorithm in ROM or in ASIC logic.

Figure 6:
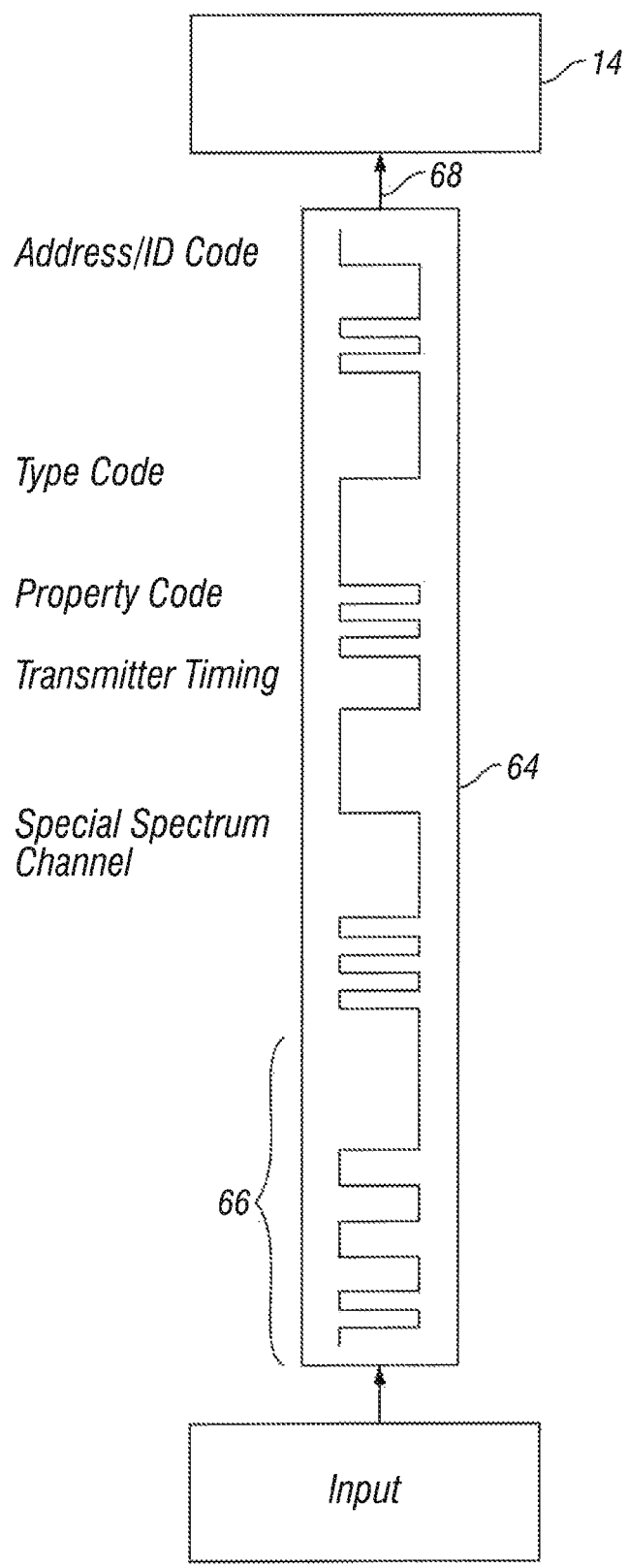
FIG. 6 is a block diagram of the jam command and security/randomization bits of the secure sensor/transmitter array of FIG. 7.

Referring to FIG. 6, the algorithm is applied to outgoing programming data 64 from system 32 and produces a number of security/randomization bits 66 that can be appended to the outgoing programming message or message 68 and sent to a sensor 14.

Figure 7:
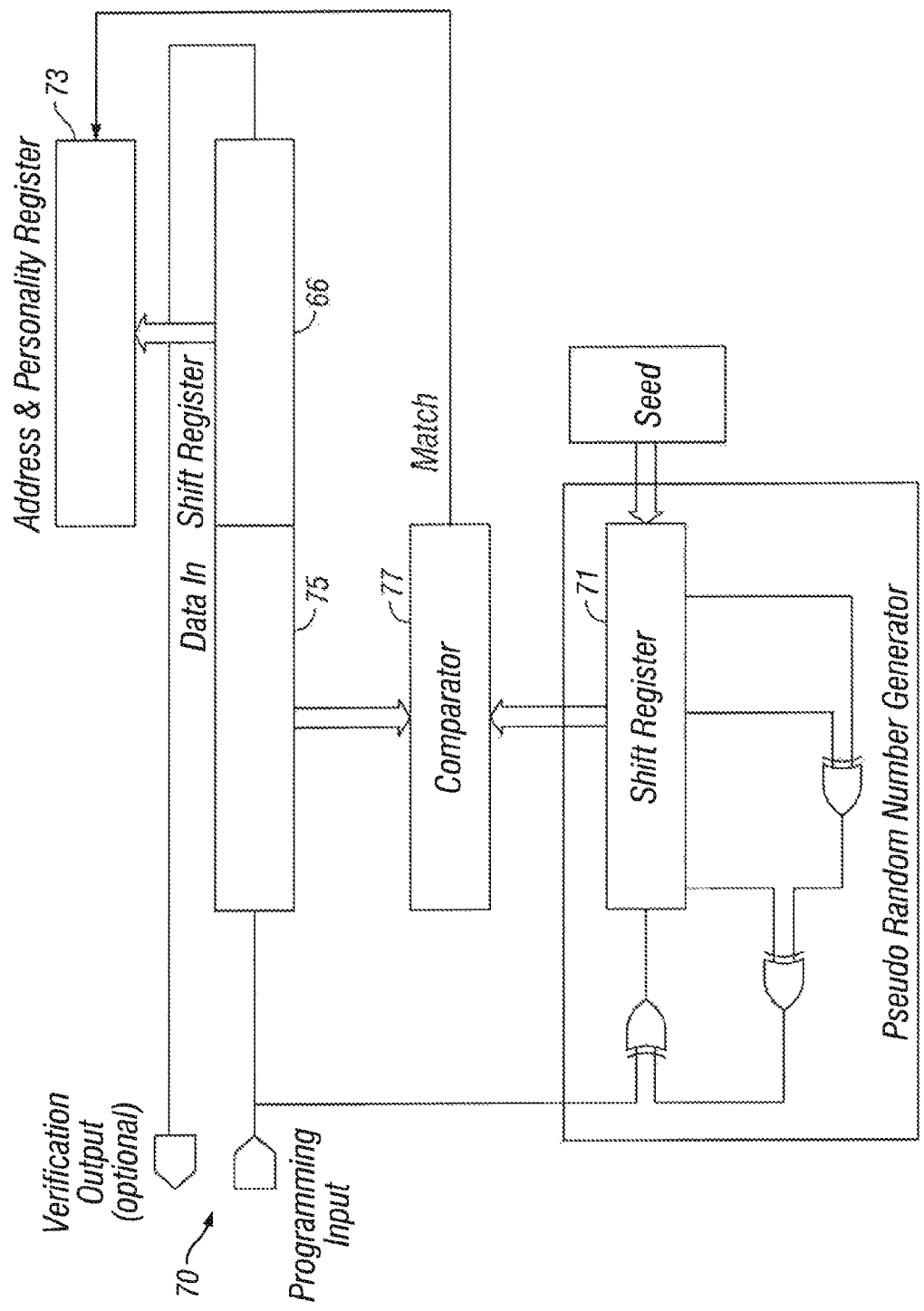
FIG. 7 is a logic circuit diagram of the sensor/transmitter programming input schematic in one embodiment of the present invention.

Referring to FIG. 7 the sensor 14 likewise applies this pseudo randomization algorithm as the security/randomization bits 66 to the outgoing programming data, now forming the incoming programming data 70 to sensor 14 and produces a several bit result in the shift register 71. The scrambling algorithm is devised such that a small difference in the programming bit stream causes a great difference in the pseudo randomization result. As a non-limiting example, the present invention can use a 16 bit polynomial to produce this pseudo randomization.

Optionally, in one embodiment, before a sensor 14 accepts this programming, stored in an address and personality register 73, both the pseudo random code, stored in data in a shift register 75 from system 32 and a sensor 14, in a shift register 71 must match via a comparator ID, 77, indicating unauthorized acceptance use. In addition to insuring authorized access, this process also insures that the data itself is correct. The longer the polynomial sequence used, the greater the security.

In one embodiment, spread spectrum or other RF transmission is used and can include programming to determine that the frequency or spread spectrum code is unique to the area. If a spread spectrum code, system code, or frequency channel is found to be occupied at a future time of use. Re-programming of the patient monitoring device 10 is then done with a new, unused spread spectrum code or system code or frequency channel can be selected, or, in the alternative, CPU 20.

As illustrated in FIG. 5, step "E" would include, for example, the step of the sensor 14, inputting the programming message and saving a seed in memory 62; with the sensor 14 utilizing the seed to code digital data bits transmitted.

Figure 8:
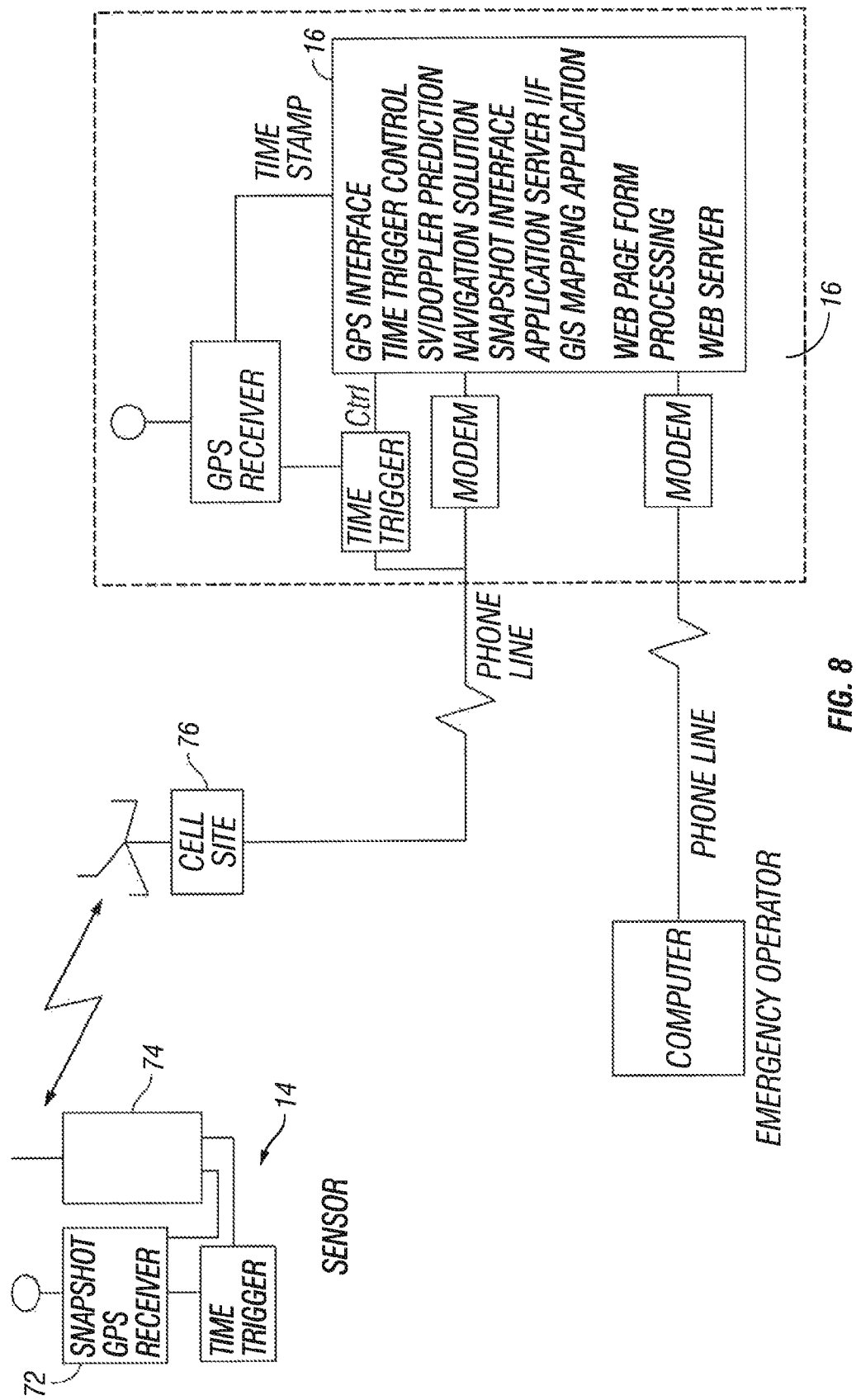
FIG. 8 is a block diagram of an embodiment of a computer implemented system for determining the location of a remote sensor utilizing the methods of the present invention.

As illustrated in FIG. 8, the location of a patient monitoring device 10 with the ID and sensors 14 can be determined. As a non-limiting example, in one embodiment the patient monitoring device 10 includes a sensor 14 that can provide a position signal having positioning data (e.g., raw GPD data or pseudo ranges) and the ID is transmitted from the patient monitoring device 10 to system server 16. Server 16 receives the position signal and analyzes the signal to generate information representing the location of the patient monitoring device 10. Server 16 transmits this location information to a client computer where the location of the patient monitoring device 10, allowing a user to identify the location of the remote sensor 14.

In one embodiment, the position signal transmitted by the remote sensor 14 can also include an emergency code. For example, in the event of an emergency, such as a medical emergency or otherwise, a user may press a "panic button" that can be on the patient monitoring device 10 or by use of a user's mobile device. Pressing the panic button may cause mobile device 74 to transmit an emergency signal to a cell site 76 where the emergency signal is relayed to server 16. In response, server 16 can transmit Doppler information regarding in-view satellites, a fix command and a time trigger signal to the patient monitoring device 10.

When the location of the patient monitoring device 10 has been determined, software running on server 16 configures server 16 such that a call or other signal is sent to a local emergency operator in the vicinity of remote sensor 14. When the call or signal is received at the emergency operator station, the location of remote sensor 14 is transmitted and displayed. In some cases, where separate panic buttons are available for identifying medical, police, fire or other types of emergencies, the nature of the emergency is also displayed for the emergency operator. Based on this information, the emergency operator can initiate an emergency response by providing the location of remote sensor 14 to the required emergency service (police, fire department, ambulance service, etc.). In other embodiments, instead of or in addition to a position report for the remote sensor 14, the emergency operator may also be provided with information which identifies an emergency response vehicle in close proximity to remote sensor 14.

Figure 9:
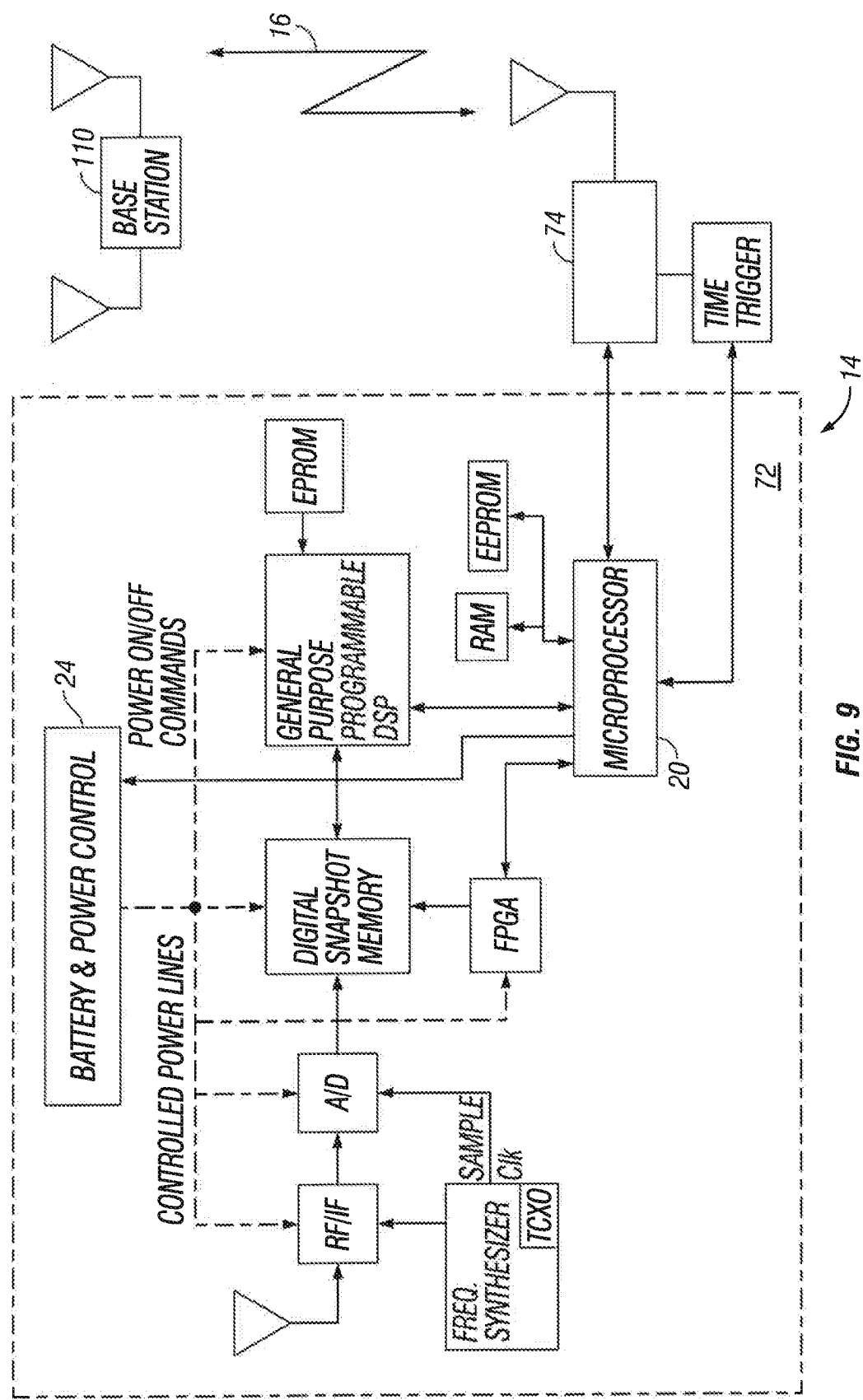
FIG. 9 is a block diagram illustrating one embodiment of a SNAPSHOT GPS receiver for use according to the present invention.

As illustrated in FIG. 9, a sensor 14 of the patient monitoring device 10 can include a SNAPSHOT GPS receiver 72. As described above, sensor 14 uses information transmitted from separately located base station 110, mobile devices, computers, and other devices, to assist in determining the position of the remote sensor 14, as more fully disclosed in U.S. Pat. No. 6,661,372, incorporated herein by reference.

As non-limiting examples, and as illustrated in FIG. 10, the sensors 14 can be a thermal transducer 78, an acoustic transducer 80, and a magnetic transducer 82. It will be appreciated that the present invention is not limited The transducers 78, 80, and 82 in the patient monitoring device 10 can communicate with a microprocessor 84 also located in the patient monitoring device 10. The patient monitoring device 10 can communicate with other devices via an RF transceiver 86, an IRDA transceiver 88, and/or an RF backscatter transceiver 90. Each of the components in the patient monitoring device 10 receives power as necessary from the battery 24, which may include the rechargeable battery.

The acoustic transducer 80 may include a microphone, a low-pass filter, a gain amplifier, and a threshold comparator. The acoustic transducer 80 may include an omnidirectional microphone, although any other suitable acoustic transducer device would suffice. The microphone may be a surface mount MEMS device that has a frequency range of 100 Hz to 10 kHz. A single MCP602 operational amplifier is used on the acoustic sensor to amplify and low-pass filter the acoustic signal from the microphone. Another operational amplifier is used to generate a voltage reference used for single biasing and detection. The microphone output is biased to the midway point between the circuit supply voltage and ground to allow for both positive and negative signal swings. The biased signal is filtered with a second order low-pass Butterworth filter to remove upper frequency noise. It is then amplified with an adjustable gain that is controlled by a digital resistor potentiometer. This digital resistor operates on an I2C bus and is controlled by the microprocessor 84. Lastly, the amplified acoustic signal is threshold detected against a static voltage to detect sufficiently large acoustic signals. The digital output of the threshold detector is connected to the microprocessor 84 for processing.

The magnetic transducer 82 can include a magnetic sensor integrated circuit, a differential instrumentation amplifier, a low-pass filter, two gain amplifiers, and a threshold detector. The magnetic transducer 82 may include an NVE AA002-02 GMR (giant magneto resistive) field sensor, although any suitable magnetic sensor would suffice. This sensor has a saturation field of 15 Oe, a linear range of 0 to 10.5 Oe, and a sensitivity of 3 mV/V/Oe. Two MCP602 CMOS operational amplifiers are used on the magnetic sensor to amplify and low-pass filter the analog output signal. An INA122UA instrumentation amplifier is used as a difference amplifier for the differential output from the magnetic sensor. The magnetic sensor IC can be based on Spintronics technology. Its output includes a differential voltage pair proportional to the detected magnetic field. The differential voltage pair is amplified and converted to a single voltage by the instrumentation amplifier. The AC-coupled signal is then amplified and filtered with a low-pass filter to remove upper frequency noise and boost the low-voltage signal output. The signal is amplified a second time by an adjustable gain controlled by a digital resistor similar to the acoustic sensor. Lastly, the amplified magnetic signal is threshold detected against a static voltage, to detect sufficiently large changes in magnetic fields. The digital output of the threshold detector can be connected to the microprocessor 84 for processing.

A DS1803E-010 digitally controlled 10 kOhm variable resistor can be used in both the acoustic and magnetic sensor circuits. It is used to adjust the gain of one gain stage in each circuit. The digital resistor is controlled through an I2C interface. A LMV393IPWR comparator is also used in both the magnetic and acoustic sensor circuits for determining when a sufficiently strong sensor signal has been detected. It compares the analog sensor signal against the voltage reference and its output is tied to the microprocessor 84 for data collection.

The thermal transducer 78 may include a Burr Brown TMP100NA/250 12-bit digital temperature sensor, although any suitable thermal sensor would suffice. The digital temperature sensor has an operating range of −55 to +120.degree. C., an accuracy of 0.5.degree. C. and a maximum resolution of 0.0625.degree. C.

Even though it is a 12-bit sensor, suitable results are achieved with only 9-bit conversions with only the 8 most significant bits used. The sensor has an I2C interface and is normally kept in sleep mode for low power operation. When directed by the microprocessor 84, the thermal transducer can perform a 9-bit temperature conversion in 75 milliseconds.

Figure 11:
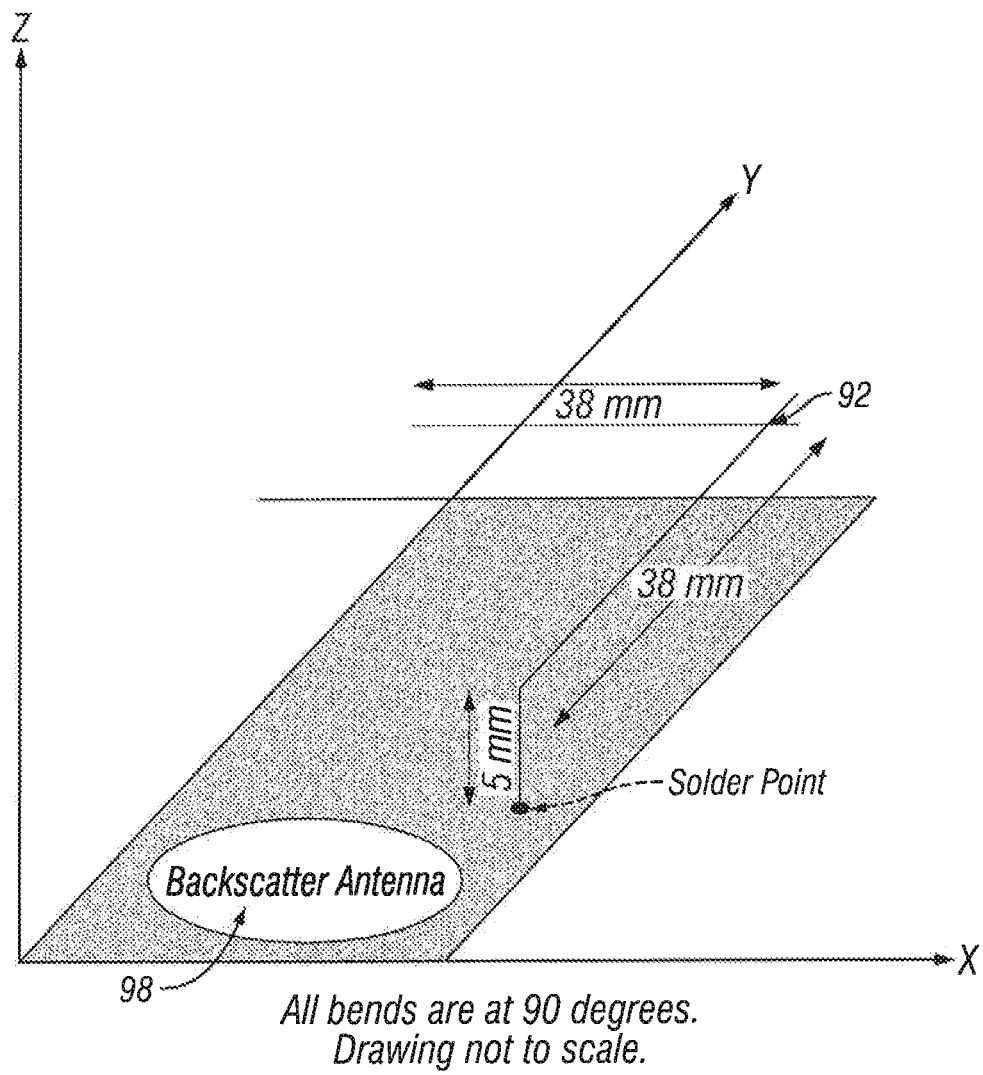
FIG. 11 is a diagram of the active RF and RF backscatter antennas.

The RF transceiver 86 may include an RF Monolithic DR3000 transceiver, although any suitable transceiver or separate transmitter and receiver 34 would suffice. This transceiver 86 allows for both digital transmission and reception. The transceiver 86 can have an operating frequency of 916.5 MHz and is capable of baud rates between 2.4 kbps and 19.2 kbps. It can use OOK modulation and has an output power of 0.75 mW. It also can use digital inputs and outputs for direct connection with the microprocessor 84. The transceiver 86 can use an antenna 92 (FIG. 11) that may include a 17 mil thick plain steel electric guitar G-string cut to a length of 8.18 cm. It is used in a monopole over ground configuration and can require a matching circuit of one inductor and one capacitor. Alternatively, Frequency Shift Keying (FSK), Quadrature Phase Shift Keying (QPSK), or any other suitable modulation scheme may be utilized.

The IRDA transceiver 88 may include a Sharp GP2W0110YPS infrared transceiver, although any suitable IRDA compliant infrared transceiver would suffice. This transceiver 88 can be IRDA v1.2 compliant and in one embodiment has an operating range of 0.7 meters. In one embodiment, it is capable of 115.2 kbps data speeds.

The RF backscatter transmission device 90 may include circuitry available from Alien Technology (of Morgan Hill, Calif.) for receiving and transmitting signals via RF backscatter. Battery 24 may be a 3.6 volt ½ AA lithium battery with a capacity of 1.2 amp hours. The battery 24 can be a power source 24 that can include a Texas Instruments TPS76930DBVT voltage regulator to regulate the output signal to 3 volts and with a maximum current of 100 mA. The voltage regulator can include a LDO.

The RF backscatter transceiver 86 in the patient monitoring device 10 communicates with an RF backscatter reader 94 such as a class 3 reader from Alien Technology. The reader 94 transmits data to the backscatter transceiver 90 of the patient monitoring device 10 by broadcasting encoded RF pulses and receives data back from the transceiver 86 by continually broadcasting RF energy to the sensor 10 and monitoring the modulated RF reflections from the sensor 10.

The RF backscatter transceiver 90 can include a printed circuit board (PCB) patch antenna for RF reception, and RF modulation, a Schotky diode detector circuit, a comparator circuit for signal decoding, and a logic circuit for wake-up. The logic circuit monitors the incoming data, and when an appropriate wake-up pattern is detected, it triggers the microprocessor 84 so that data reception can begin. In one embodiment, the reader 94 has an operating frequency between 2402 MHz and 2480 MHz, and uses frequency hopping in this band to reduce noise interference. A modulation method used by the reader 94 can be On-Off Keying (OOK). In one embodiment, the transmission power is 1 watt. The operation of the reader 94 may be controlled by an external computer (not shown) as directed by Labview software via a RS-232 serial link.

The RF transceiver 86 can communicate with an external RF transceiver 96 such as a DR3000 transceiver from Radio Monolithics, Inc. In one embodiment, it operates at 916.5 MHz, uses OOK modulation, has a communication range of 100 meters line of sight, and a baud rate of 19.2 kbps. The active RF antenna 92 can be a quarter-wavelength monopole made from a guitar G-string and appropriate matching circuitry. Two control lines from the microprocessor 84 can be used to select the mode of operation, choosing from transmit, receive, and sleep. The active RF receiver 34 consumes the most power in receive mode compared to the other two communication links.

FIG. 6 shows the relative positioning and shape of the active RF antenna 92 and the RF backscatter antenna 98.

The IRDA transceiver 88 of the patient monitoring device 10 can communicate with an external IRDA transceiver 100 that may be identical to the IRDA transceiver 88. Alternatively, the IRDA transceiver 100 can be one such as is provided in most personal digital assistants (PDA) as well as many other consumer devices. The IRDA communication link follows the standard IRDA signal and coding protocol and is modeled after a standard UART interface. In one embodiment, the IRDA transceiver 88 is capable of data speeds less than 115.2 kbps, and may only have a range of 0.7 meters for transmission. One advantage of the IRDA communication link is that it does not require any of the RF spectrums for operation, but it typically does require line-of-sight communication.

When any one of the transceivers 86, 88 and 90 on the patient monitoring device 10 detect the beginning of valid data on their respective communication link, all other transceivers are disabled, thereby preventing the corruption of incoming data with the noise or partial data packets on the other communication links. However, if the data on the active transceiver proves to be erroneous, the other transceivers will be re-enabled if appropriate to allow normal operation to continue. If the data received by the active transceiver is valid, however, the other transceivers will remain disabled for several hundred milliseconds longer in the high probability that the next data packet will be transmitted on the same communication link. If, after this extended delay, no additional packets are received, then the other transceivers will be re-enabled as appropriate.

In one embodiment, the active RF protocol has no wake-up or synchronization packets, and the packets sent to and from the sensor are identical. In one embodiment, the format of an active RF packet is shown in FIG. 2. It can include a preamble to reset and spin-up the state machine of the RF receiver 34 and to properly bias the receiver's 34 data slicer/threshold detector for optimum noise rejection and signal regeneration, two framing bits to indicate the beginning and end of the data bytes, and the data bytes themselves.

Figure 12:
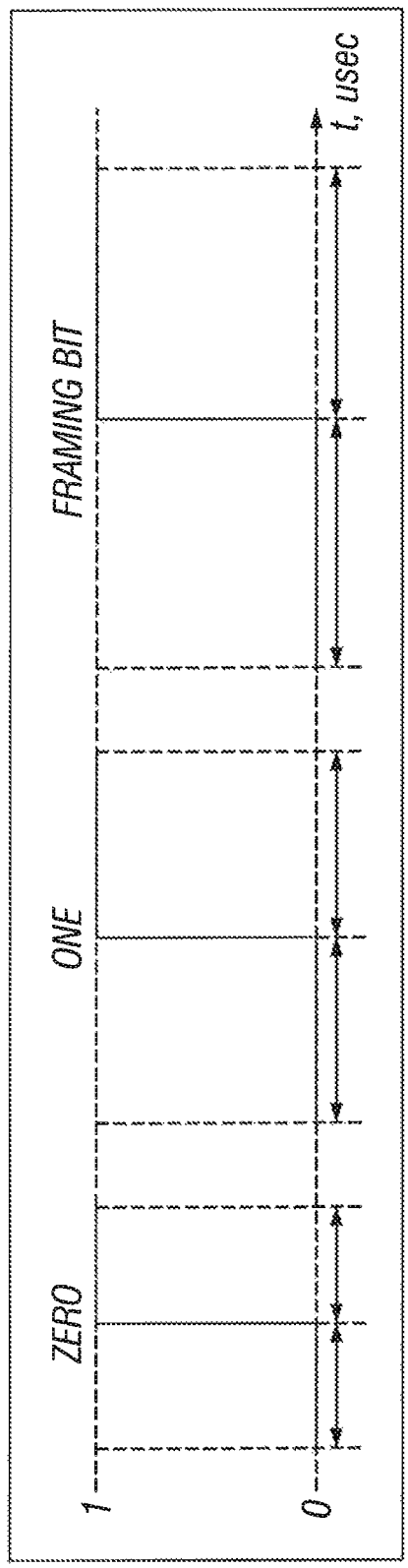
FIG. 12 is a diagram of the encoding scheme for the symbols in the active RF protocol.

Furthermore, the encoding scheme for the three symbols is shown in FIG. 12. The entire packet is DC balanced to maintain an optimal level on the data slicer/threshold detector and the receiver 34. Data is sent most significant bit first.

Figure 13:
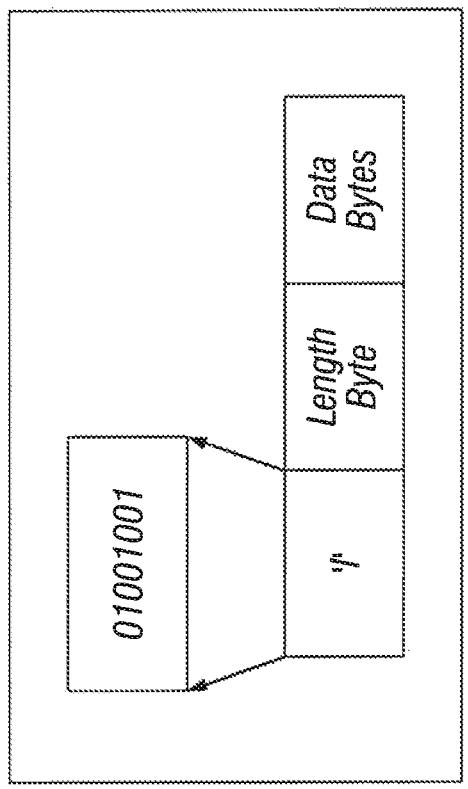
FIG. 13 is a diagram of the packet structure in the IRDA protocol.
Figure 14:
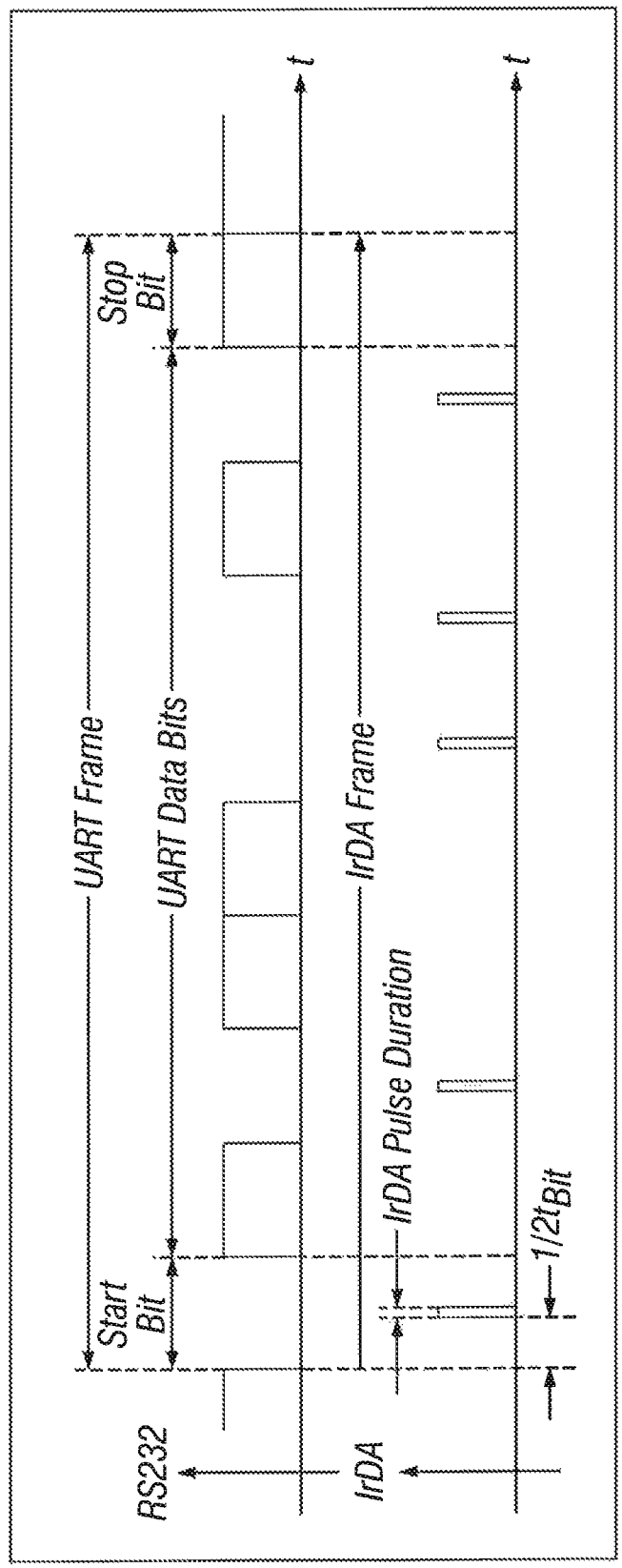
FIG. 14 is a diagram of the encoding scheme in the IRDA protocol.

The IRDA communication link can follow the standard IRDA protocol for bit encoding and UART protocol for byte transmission. Packets transmitted on the IRDA link can contain no preamble or framing bits, but they do have a header that contains two bytes. The first byte is an ASCII "I" which denotes the beginning of a valid IRDA packet. The second byte equals the number of preceding bytes in the packet. This value is used by the receiver 34 to determine when the entire packet has been received and processing of information can begin. The packet structure is shown in FIG. 13 and the IRDA/UART encoding scheme is shown in FIG. 14.

The data bytes contained in a packet transmitted to the sensor 10 through any of the communication links conform to a packet format. The CMD section of a packet is a single byte that identifies the type of packet being sent. The CMD byte appears above the beginning and end of the packet and the two must be identical. The reason for including the redundant byte is to further eliminate the chance of a packet's CMD identifier being corrupted at the receiver 34, even if the CHECKSUM is correct.

The PAYLOAD contains all of the data that must be sent to, or returned from, the sensor. The PAYLOAD is broken down into individual bytes with the overall number of bytes and their content dependent on the type of packet being sent.

The CHECKSUM is a 16-bit CRC that is performed on all bytes in the data packet excluding the end CMD byte in packets generated by the external device. The CHECKSUM is sent most significant byte first.

The transceivers 86, 88 and 90 may be required to communicate over a greater distance than do the components described herein. Upgrading these components to be suitable for longer distance transmission is considered to be within the spirit of this invention. The type of transducer is not limited to the specific transducer types described herein. In addition, the logic described herein for arbitrating between which communication device to use to communicate with the outside world and which sensor data to provide at what time is but one possible approach to arbitration logic within such a remote sensor 10.

Figure 15:
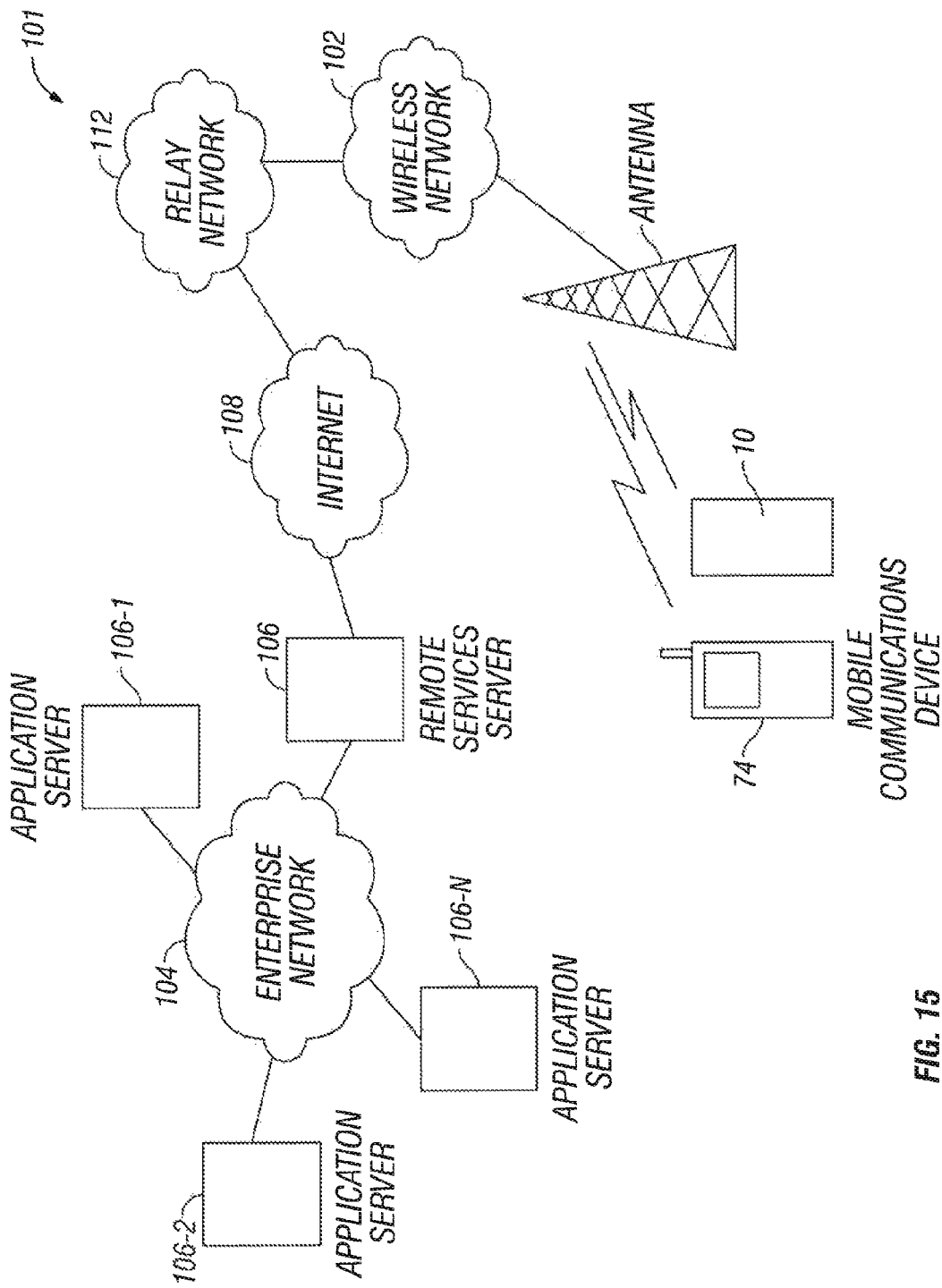
FIG. 15 illustrates one embodiment of a wireless network that can be used with the present invention.
Figure 16A:
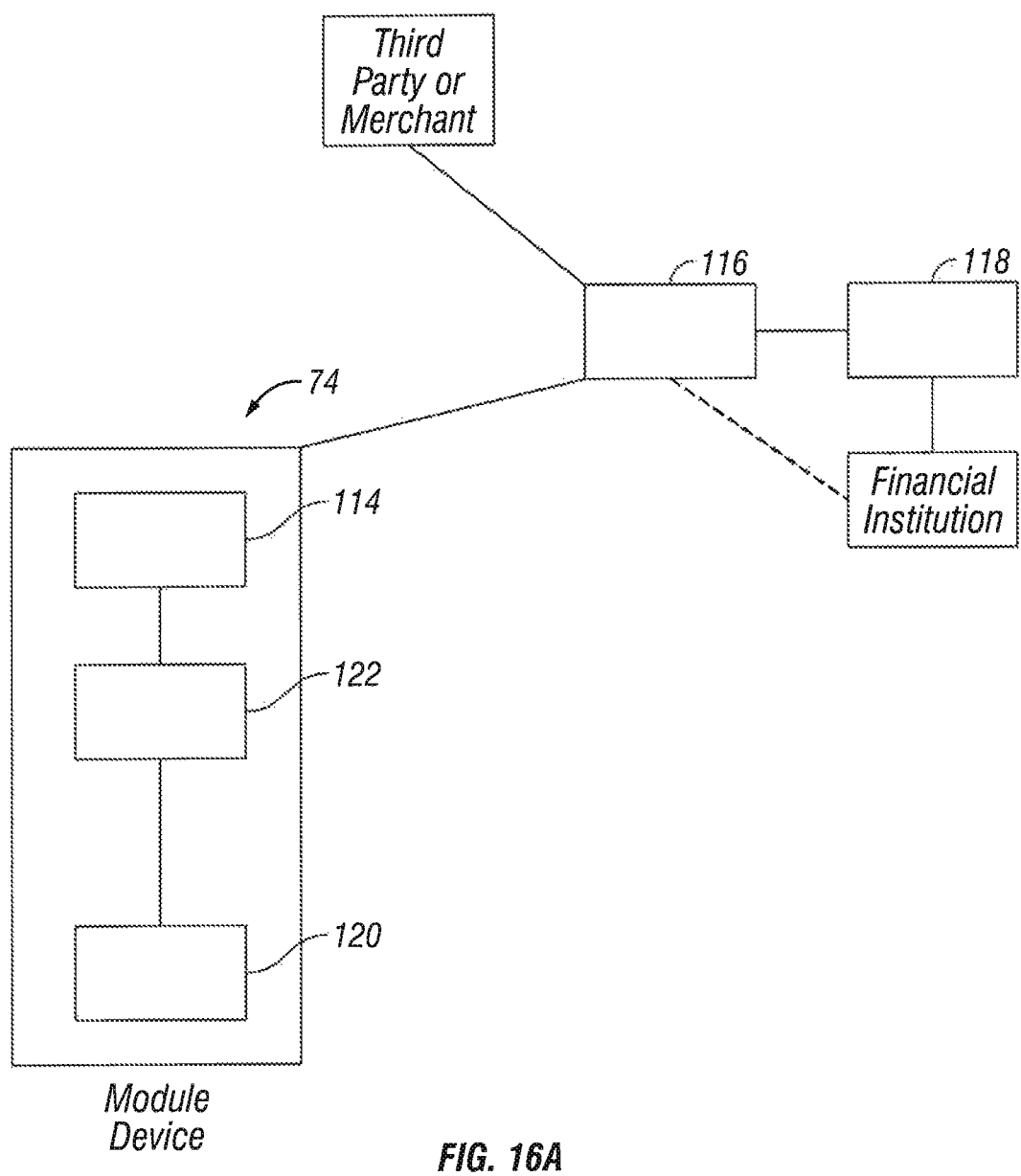
FIGS. 16(a)-16(d) illustrate various embodiments of the interaction of a wearable device of the present invention with an interaction engine, a transaction engine, a decoding engine, and a payment system and a third party.
Figure 16B:
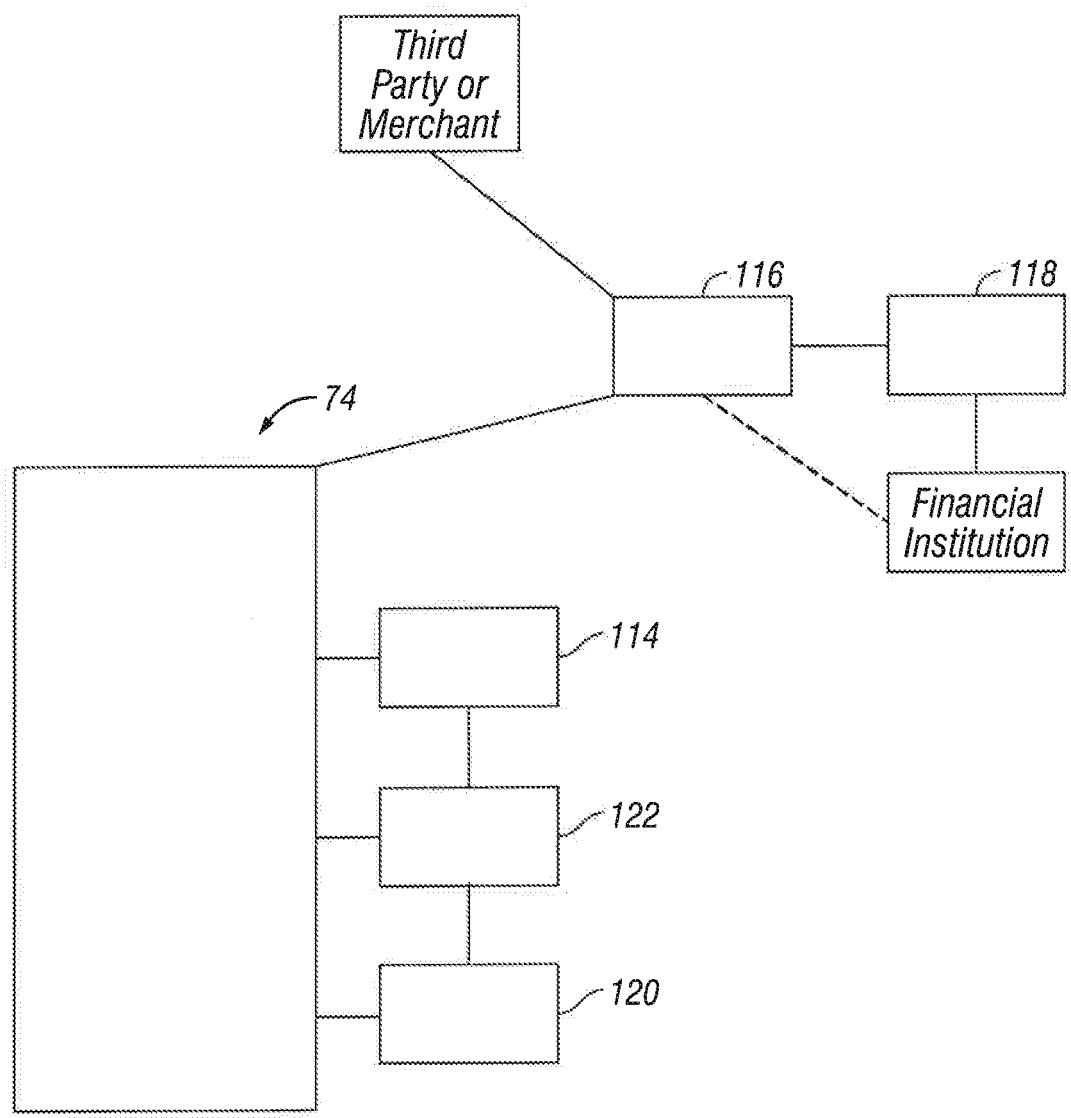
Figure 16C:
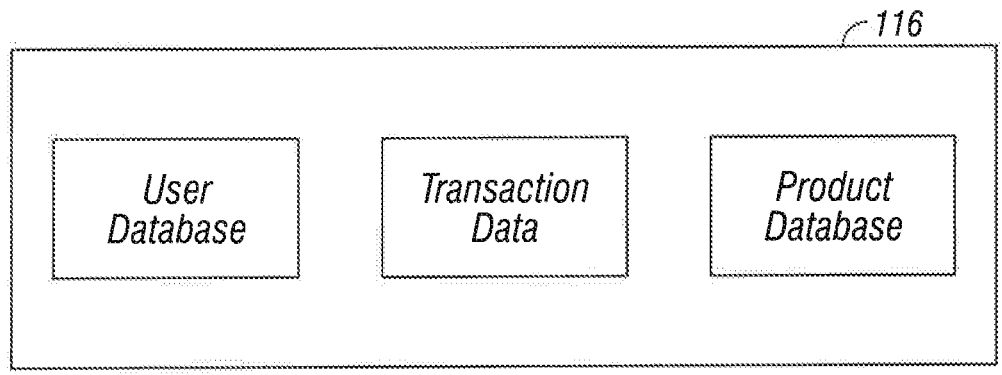
Figure 16D:
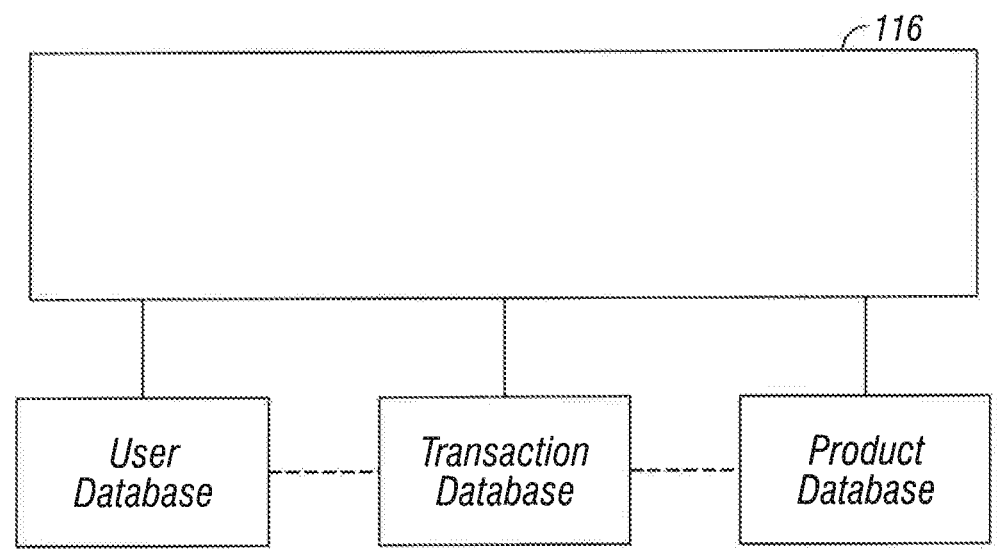

FIG. 15 illustrates one embodiment of an exemplary network 101 that can be used with the present invention. As shown in FIG. 15 a wireless packet data service network 102 that can be utilized with the patient monitoring device 10. An enterprise network 104, which may be a packet-switched network, can include one or more geographic sites and be organized as a local area network (LAN), wide area network (WAN) or metropolitan area network (MAN), and the like. One or more application servers 106-1 through 106-N can be included and disposed as part of the enterprise network 104 are operable to provide or effectuate a host of internal and external services such as email, video mail, Network Systems access, corporate data access, messaging, calendaring and scheduling, information management, and the like using the unique IDs of the wearable devices 10. The patient monitoring device 10 can be in communication with a variety of personal information devices other than the patient monitoring device 10, including but not limited to, computers, laptop computers, mobile devices, and the like.

Additionally, system server 16 may be interfaced with the enterprise network 104 to access or effectuate any of the services from a remote location using a patient monitoring device 10. A secure communication link with end-to-end encryption may be established that is mediated through an external IP network, i.e., a public packet-switched network such as Network Systems 108, as well as the wireless packet data service network 102 operable with a patient monitoring device 10 via suitable wireless network infrastructure that includes a base station (BS) 110. In one embodiment, a trusted relay network 112 may be disposed between Network Systems 108 and the infrastructure of wireless packet data service network 102.

In another embodiment, the infrastructure of the trusted relay network 112 may be integrated with the wireless packet data service network 102, and the functionality of the relay infrastructure can be consolidated as a separate layer within a "one-network" environment. Additionally, as non-limiting examples, patient monitoring device 10 may be capable of receiving and sending messages, web browsing, interfacing with corporate application servers, and the like, regardless of the relationship between the networks 102 and 112. Accordingly, a "network node" may include both relay functionality and wireless network infrastructure functionality in some exemplary implementations.

In one embodiment, the wireless packet data service network 102 is implemented in any known or heretofore unknown communications technologies and network protocols, as long as a packet-switched data service is available therein for transmitting packetized information. For instance, the wireless packet data service network 102 may be comprised of a General Packet Radio Service (GPRS) network that provides a packet radio access for mobile devices using the cellular infrastructure of a Global System for Mobile Communications (GSM)-based carrier network. In other implementations, the wireless packet data service network 102 may comprise an Enhanced Data Rates for GSM Evolution (EDGE) network, an Integrated Digital Enhanced Network (IDEN), a Code Division Multiple Access (CDMA) network, a Universal Mobile Telecommunications System (UMTS) network, or any 3rd Generation (3G) network.

Referring now to FIGS. 16(a) through 16(d), in one embodiment, the patient monitoring device 10 is in communication with an interaction engine 120 that can be at a mobile device 74 or system 32. The interface engine can be a software application running on mobile device 74 associated with another party, including but not limited to a merchant, an associate, a friend, and the like. The enables the patient monitoring device 10 user and a merchant to interact with a transaction engine 114 to and enter into a financial transaction for the transfer of funds from a third party payment system 116 that is independent of the patient monitoring device 10 user's financial account 118, and complete a transaction. It should be noted that the payment system 116 can be affiliated with the financial account 118 or can be a separate and non-affiliated with the financial account 118. The interaction engine 120 can take input of information related to a transfer of funds from the patient monitoring device 10 users' financial accounts 118 as input to the transaction engine 114 to initiate and complete a financial transaction, including but not limited the purchase and payment of goods and services. In one embodiment, this input to the interaction engine 114 can include, an amount of a transaction, additional items related to the transaction, authorization and/or signature of the patient monitoring device 10 user.

In one embodiment, the mobile device 74 receives information from the patient monitoring device 10, e.g., the unique ID.

The interaction engine 120 can also present products or services provided by a merchant to directly to or through system 32 to the patient monitoring device 10 user. In one embodiment, the patient monitoring device 10 users can use the mobile device 74, the WEB, and the like, to view, text, pictures, audio, and videos, and browse through the products and services on the mobile device 74, personal computers, other communication devices, the WEB, and anything that is Bluetooth®, anything associated with Network Systems, and the like.

In one embodiment, the transaction engine 114, which can be at the mobile device 74, or external to the mobile device 74, including but not limited to patient monitoring device 10 and the like, takes decoded financial transaction card information from a decoding engine 122, internal or external to the mobile device 74, and a transaction amount from an interaction engine 120, also internal or external to the mobile device. The transaction engine 114 then contacts the payment service 116, and or the patient monitoring device 10 users' financial account 118, such as an acquiring bank that handles such authorization request, directly or through the payment system 116, which may then communicate with a financial transaction card issuing bank to either authorize or deny the transaction. The payment system 116 can include a user database, a transaction database, a product database, and the like. These databases can also be external to payment system 116. If the third party authorizes the transaction, then the transaction engine 114 transfers funds deducted from the account of the patient monitoring device 10 user, or the payment system 116 can already have those funds readily available, to an account of a third party which can be another patient monitoring device 10 user, a merchant, and the like, and provides transaction or transfer of fund results to the interaction engine 120 for presentation to a third party.

In one embodiment, the transaction engine 114 does not have the financial account or financial card information of the patient monitoring device 10 user that is doing the transfer. In some embodiments, the transaction engine 114 keeps only selected information of the patient monitoring device 10 user's financial accounts 118 or financial transaction cards.

In one embodiment, the wearable device communicates directly, without mobile device 74, with the payment system 116 and/or the user's financial account 118 or associated financial institution.

In one embodiment, the transaction engine 114 communicates and interacts with the financial account 118 or associated financial institution directly or through the payment system 116, through a user database, product database, and transaction database, which databases can be separate from or included in the payment system 116, over a network. The network can be a communication network, as recited above, and can be based on well-known communication protocols, including but not limited to, a TCP/IP protocol.

With social networking applications, the patient monitoring device 10, with its unique ID, is an ID device. Information from the patient monitoring device 10 relating to social networking, and the like, communicates with system 32. In this manner, the wearable devices 10, with their own unique ID's, can be recognized. This can occur at different locations, close by, distanced, and notifications can be sent to the different users wearing a patient monitoring device 10 for a variety of social networking and other communication applications. Additionally, patient monitoring device 10, with its sensors 14 and ID can communicate directly to social networking sites, Network Systems, cloud services, and the like.

In one embodiment, with the current permissions given by the wearable device users, marketers, companies or individuals who wish can deliver advertisement patient monitoring device 10 users. More particularly, system 32 can be configured to allow marketers, and the like, to deliver advertisements to consumers to buy products or services offered by the marketer. Advertisements can also be sent to patient monitoring device 10 users with the appropriate permissions. In one embodiment, system 32 maintains the anonymity of the patient monitoring device 10 users while allowing the marketers to have their advertisements delivered to those that fall within their defined market segment.

In one embodiment, the wearable device ID of a user provides a method of identifying and contacting users of a social networking service. The method may include the steps of signing up for a social networking service, displaying the wearable device ID, viewing another person's unique wearable device ID displayed by another user, and finding that user on a social networking service website by searching for the user using the wearable device ID viewed.

System 32 may serve a number of purposes without straying from the scope of the present invention. For example, the social networking service may allow patient monitoring device 10 users to engage in non-romantic relationships, keep in touch with acquaintances, friends and family, professional business relationships, and romantic relationships, may allow communication between wearable device users on a message board or Network Systems forum, and may allow users to follow up on missed-connections that otherwise would not have been realized.

In one embodiment, the step of providing personal information to start an account with system 10 for different applications may be performed by a purchasing or acquiring a patient monitoring device 10, with a unique assigned ID, and the user can fill in an online form. This form may require users to fill in fields on the form. These fields may include: first and last name, email address, a desired password, phone number, gender, birth date, address, geographic region, education information, employment information, interests, relationship information and interests, family information, religious views, ethnicity, physical features including hair color, eye color, measurements, and the like, type of relationship being sought, living situation, answers to quiz questions, and a personal description about interesting personality traits, among other things. In addition, users may upload one or a plurality of photographs for other users to view, or for users to store the photo or photos on the server of system 32.

In another embodiment the step of providing personal information to start an account with system 32 by patient monitoring device 10 users may be performed automatically. In this embodiment, system 32 can access a social networking service, access, via computer, contact lists or other sources of information that may include the type of information listed above.

In a further embodiment, the step of providing personal information to system 32 can be automated by importing data containing the personal information required from other social networking services including but not limited to Facebook®, LinkedIn®, MySpace®, Match.com®, EHarmony.com®, a user's email or contact list, v-card, and the like.

The unique wearable device ID may allow the user to be searched and identified by other users and potential users. Also, a computer generated email address may be provided to a user. In one embodiment, this email address may be the user's user ID followed by "@iseenya.com." In another embodiment, the email address may be the user's user ID directed to another domain name.

In one embodiment, a computer generated personal page may be provided to a patient monitoring device 10 user. The personal page may utilize a computer to automatically import the information provided when signing up with system 32 or a social networking service. In another embodiment, the information and formatting of the personal page can be customizable.

When mobile device 74 is used, it communicates with one or more sensors 14 that are at the patient monitoring device 10, as more fully herein. The mobile device can 74 pull from system 32 updates from the server 16, including but not limited to settings such as alarms, name of the wearable device wearer using the ID, a sensor 14 and the like. Sensors 14 at the patient monitoring device 10 can send streams of information, both encrypted and non-encrypted to the mobile device and then to the server at system 32. Server 16 sends encrypted, and can also send non-encrypted information, to mobile device 74. Processing of this information can be achieved at the mobile device 74, and/or server 16. Mobile device 74 can receive raw sensor information from the patient monitoring device 10. This information can be compressed as well as non-compressed. A compression algorithm, at the wearable device and/or mobile device 74 or system 32, can be used in order to minimize the amount of information that server 16 sends. System 32 can include additional encryption and/or decryption systems.

Figure 17:
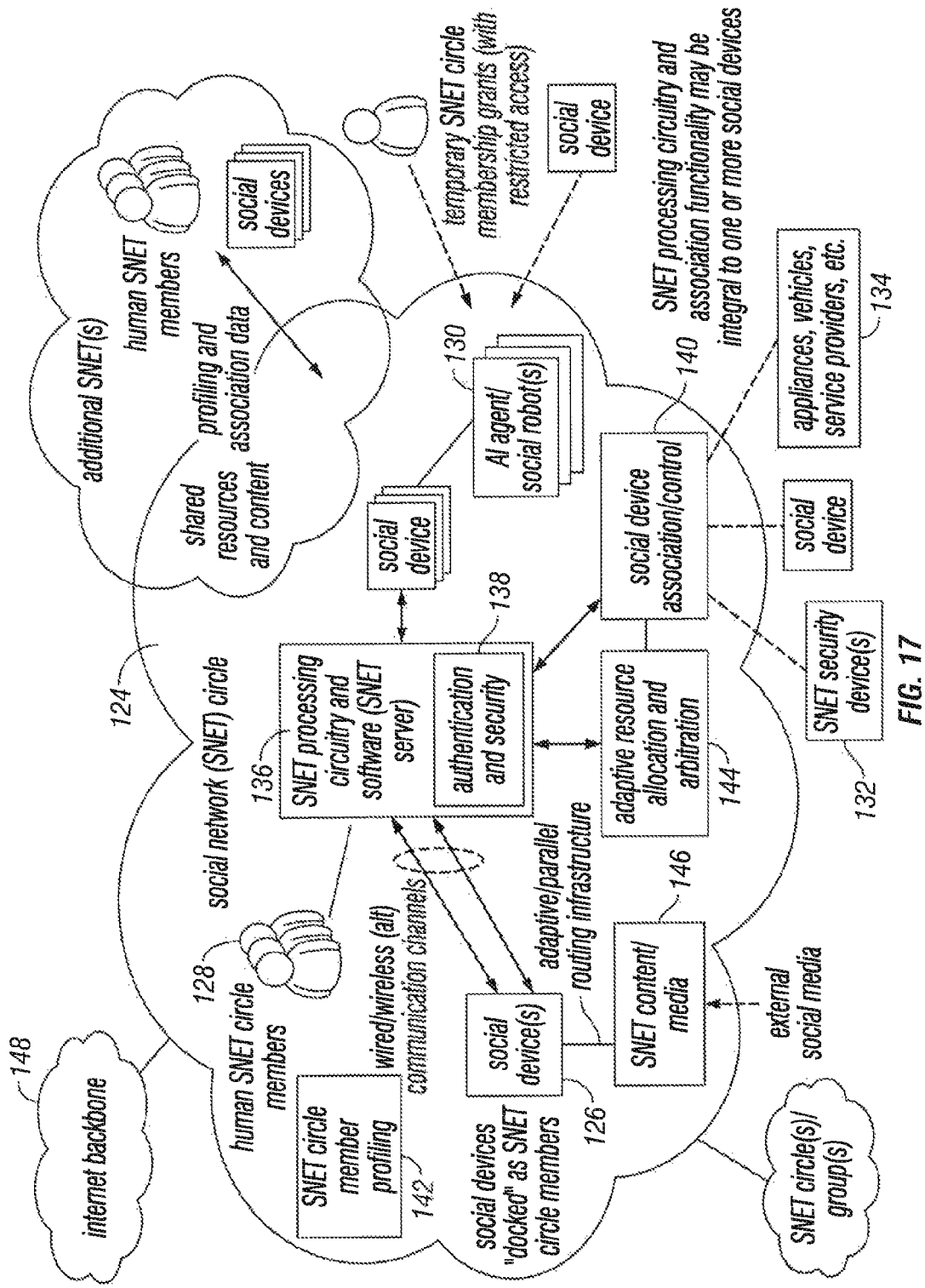
FIG. 17 illustrates an embodiment of a social network circle with social devices in accordance with one embodiment of the present invention.

Referring now to FIG. 17, a social network circle/group 124 (hereinafter "SNET circle") comprising social devices 126, including patient monitoring device 10, is shown. Beyond traditional social networking features and services, a SNET circle 124 and associated social devices 124 according to various embodiments of the invention include numerous novel features and attributes as described more fully below with general reference to the illustration. Patient monitoring device 10 can utilize network 101 for communication with the SNET circle, as well as with other social networking sites, or through system 32.

Briefly, membership in the SNET circle 124 may comprise docked and undocked social devices 124 and human SNET circle members [104] 128, as well as proxies thereof. Further, SNET circle 124 nodes may include device services and software (e.g., applications) of various types participating as members. By way of example, SNET circle members might include artificial intelligence agents/social robots 130, SNET security device(s) 132, appliances, vehicles and service providers 134, common or authorized members/functionality of other SNET circles 124, and the like. Further, access to specific content and resources of a SNET circle 124 may be shared with members of additional SNET(s) 124, including remote or web-based applications. Such access can be conditioned on acceptable profiling and association data. Similarly, social devices or individuals may be granted temporary or ad hoc memberships, with or without restricted access.

In the illustrated embodiment, formation, maintenance and operation of SNET circle 124 is performed by standalone or distributed SNET processing circuitry and software 136. It is noted that the "SNET processing circuitry" may comprise hardware, software, applications, or various combinations thereof, and be configurable to support various functionalities disclosed herein. Further, the SNET processing circuitry 136 may be included in a standalone server, server farm, cloud-based resources, network 101, system 32 and/or the various types of devices described below, and incorporate authentication and security functionality 138. In addition, specialized middleware may also be utilized by SNETs according to the invention, including standardized middleware with an associated certification process. Interactions and interdependencies within the SNET circle 124 may involve one or more of a social device association/control module 140, a SNET circle member profiling module 142, and an adaptive resource allocation and arbitration module 144 as described more fully below.

Distribution of internal and external SNET content/media 146 can be accomplished in a variety of ways in accordance with various embodiments of the invention. For example, media distribution may involve an adaptive or parallel network routing infrastructure involving a wide variety of communication protocols and wired and/or wireless communications channels. SNET content/media 146 may comprise, for example, various user-driven (advertising) channels, pictures, videos, links, online text, etc. Access to such content, as well as communications with and remote access to social devices 124 of the SNET circle 124, may occur over an Network Systems backbone 148, cellular communication system, WAN, LAN, and the like.

Figure 18:
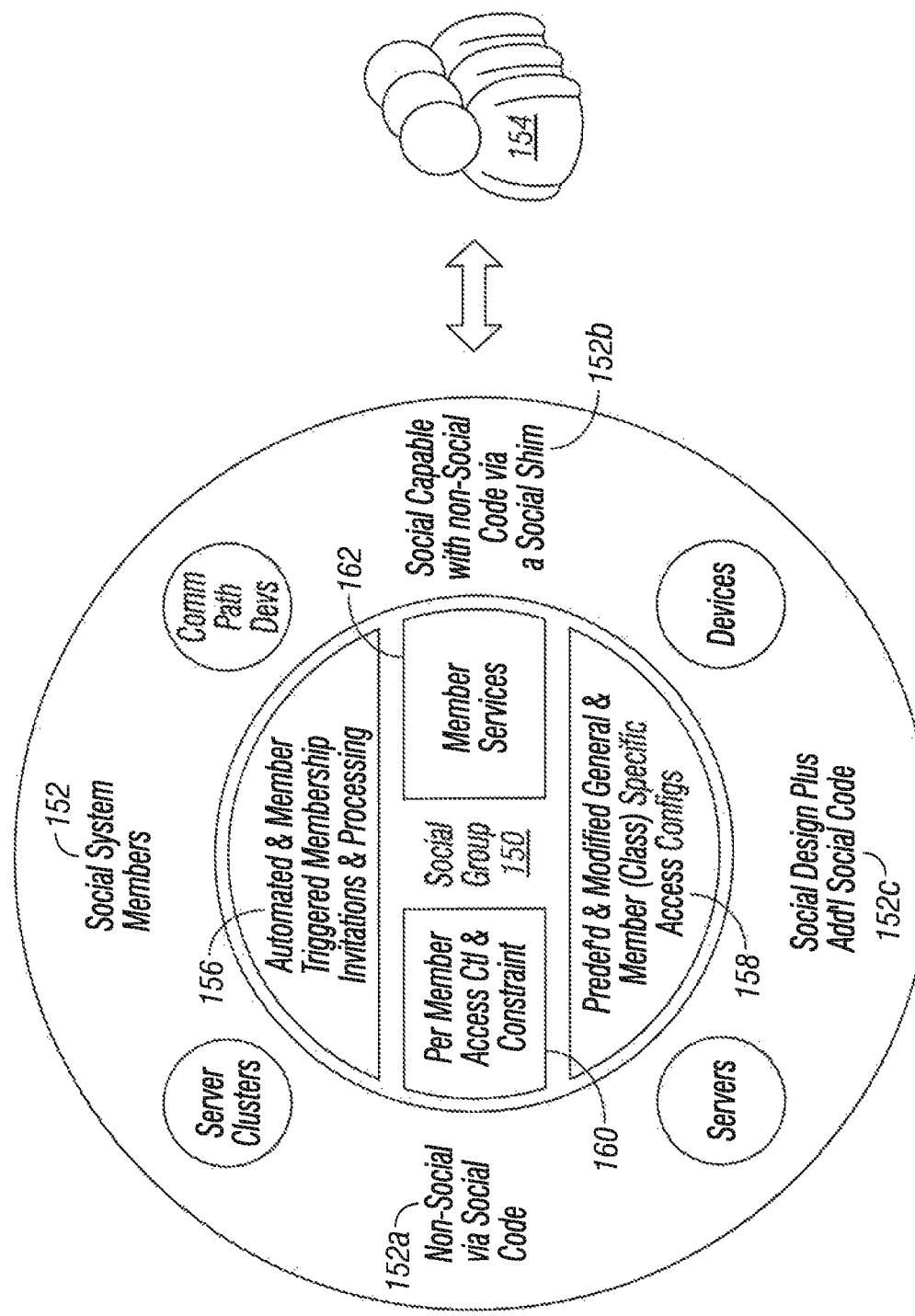
FIG. 18 illustrates an embodiment of a social group with a variety of members in accordance with one embodiment of the present invention.

FIG. 18 illustrates an embodiment of a social group 150 comprising a variety of members in accordance with the present invention that can communicate through their wearable devices 10 and other devices, including but not limited to mobile devices 74. In this embodiment, membership in the social group 150 may include a variety of novel social system members [204] 152 functioning in various capacities within the social group 150. As will be understood, certain of the social system members 152 may support direct or indirect associations between the social group 150 and human members/non-members and users 154.

In the illustrated embodiment, social system members (or nodes) 152 include one or more local or remote servers and server clusters that provide a support infrastructure for social group functionality and member operations (routing, data storage, services, etc.). Communications within the social group and with non-members may occur via dedicated or multi-function communication path devices.

Social system members 152 further include devices configured to operate as nodes within the social group 150. Social functionality in such devices and other social system members 152 can be implemented through various means. For example, a device may have integral hardware/firmware/software to support social group access and member operations. Alternatively, a general purpose device 152a may include social code that enables participation in the social group 150. In a further embodiment, a device 152b designed to include social functionality may participate in the social group 150 through a combination of non-social code and a social shim layer or driver wrapper. In yet another embodiment, a member device 152c having a social design may utilize additional social code, including code specific to a social group 150.

Participation in the social group 150 is supported through functionality that includes automated and member-triggered membership invitations and processing (membership management) 156. More particularly, membership management 156 may function to invite prospective members to participate in the social group 150 through automatic, automated and member-triggered processes. For example, membership management 156 might be configured by a human user 154 to establish a social group 150 by automatically inviting/accepting social system members having certain characteristics (such as devices owned or controlled by the user or acquaintances of the user).

Processing of accepted invitations and unsolicited requests to join the social group 150 may be conditioned upon input or authorization from an existing social system member(s) 152 or human user(s) 154 (e.g., through a user interface). Similarly, membership management 156 may be configured to generate automated suggestions regarding which prospective members receive an invitation. Various other approaches, such as those described herein, can be used to establish membership in accordance with the invention.

Access to and visibility of resources of a social group 150, including services and data, may be managed through general and member class-specific access configurations 158. For example, if membership in the social group 150 includes family members and associated devices, a uniform access configuration (or separate device and human configurations) could be applied across the class in an automatic or automated manner. In other embodiments, access control and constraints are imposed on a per-member basis.

The social group 150 may offer a wide variety of member services 162, including both internal and external services accessible by social system members 152. By way of example, the social group 150 may offer email or other communication services between full members and/or authorized guest members and visitors. As with other resources of the social group 150, access control and constraints on member services 162 may be applied to individual members or classes of members.

Figure 19:
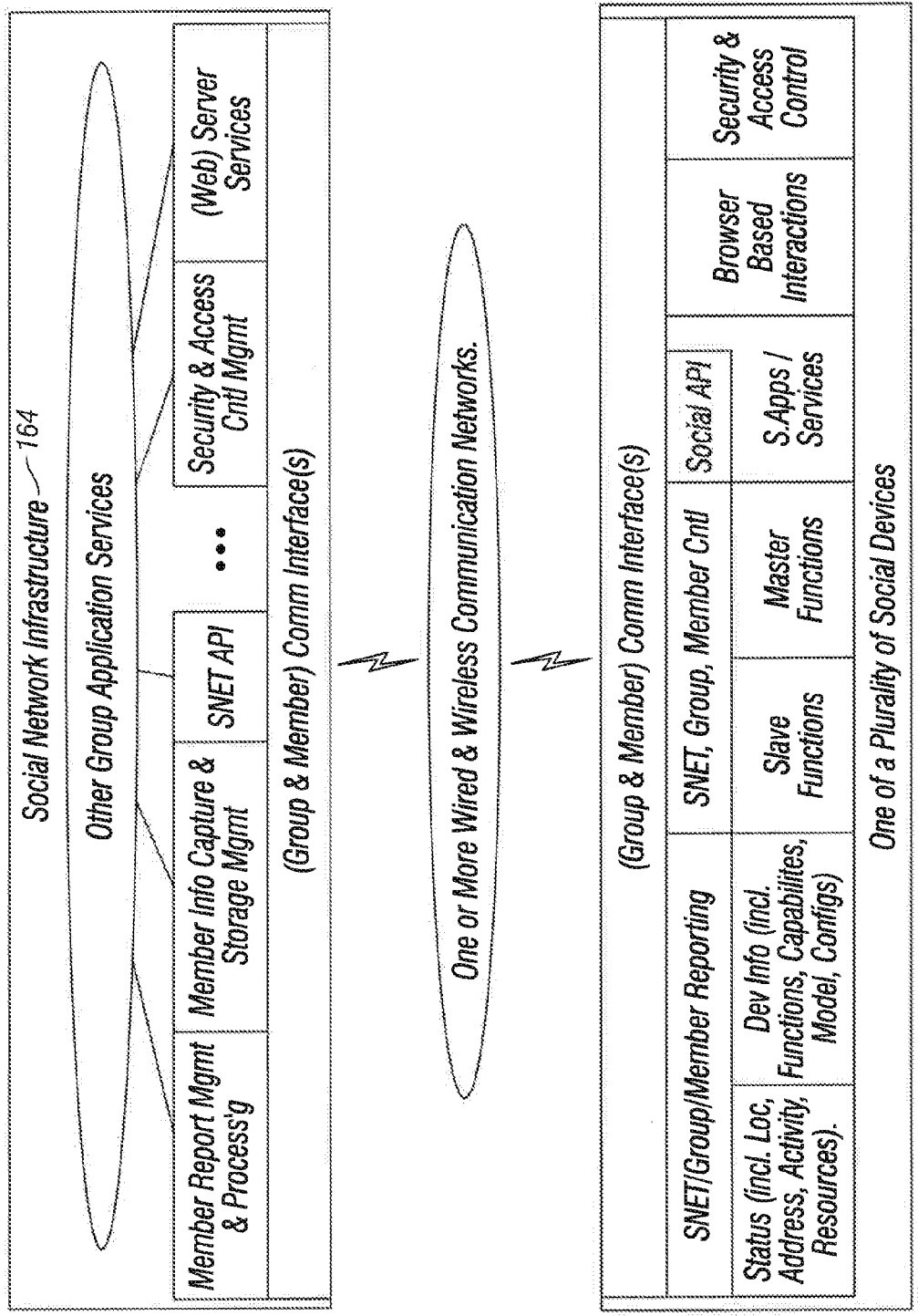
FIG. 19 is a functional block diagram illustrating a social network infrastructure and social devices in accordance with one embodiment of the invention.

FIG. 19 is a functional block diagram illustrating a social network (SNET) infrastructure 164, as more fully described and disclosed in EP 2582116, fully incorporated herein by reference.

Figure 20:
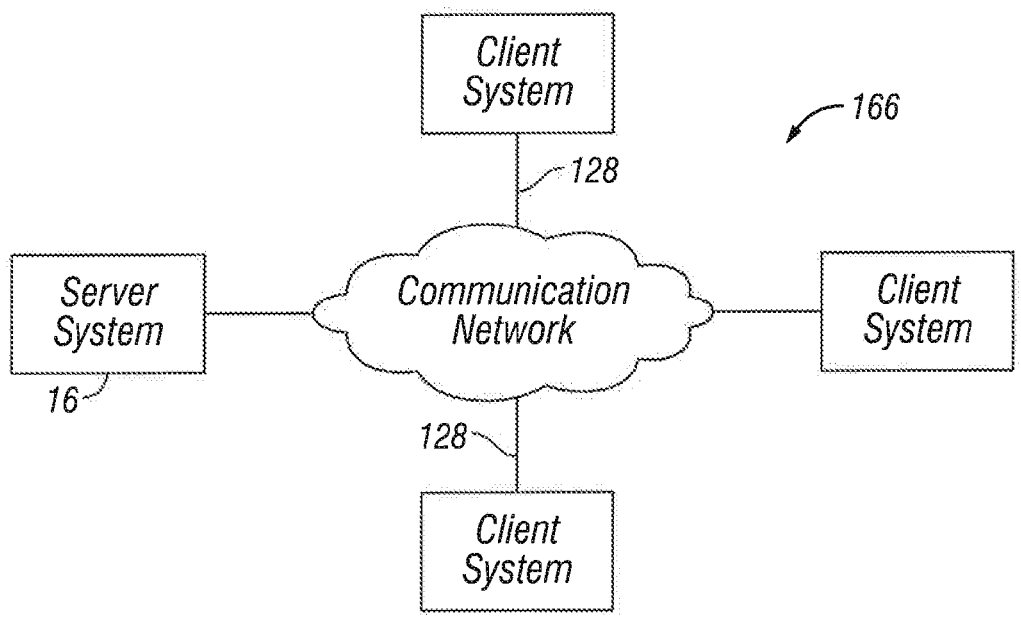
FIG. 20 illustrates a simplified block diagram of a client-server system and network in one embodiment of the present invention.

In one embodiment, illustrated in FIG. 20, wearable devices 10 are in communication with a distributed computer network 166 that can include networks 102, 104, 112, coupled to Network Systems 108 and system 32 via a plurality of communication links 168. Communication network 166 provides a mechanism for communication with system 16, patient monitoring device 10, social media networks, mobile devices 74, payment systems, 116, the engines 114, 120, 122, components of system 16, and with all third parties, as described above.

The communication network 166 may itself be comprised of many interconnected computer systems and communication links. Communication links 168 may be hardwire links, optical links, satellite or other wireless communications links, wave propagation links, or any other mechanisms for communication of information. Various communication protocols may be used to facilitate communication between the various systems shown in FIG. 20. These communication protocols may include TCP/IP, HTTP protocols, wireless application protocol (WAP), vendor-specific protocols, customized protocols, and others.

While in one embodiment, communication network 166 is the Network Systems, in other embodiments, communication network 166 may be any suitable communication network 166 including a local area network (LAN), a wide area network (WAN), a wireless network, an intranet, a private network, a public network, a switched network, and combinations of these, and the like.

System 32 is responsible for receiving information requests from wearable devices 10, third parties, and the like, performing processing required satisfying the requests, and for forwarding the results corresponding to the requests backing to the requesting patient monitoring device 10 and other systems. The processing required to satisfy the request may be performed by server 16 or may alternatively be delegated to other servers connected to communication network 166.

Figure 21:
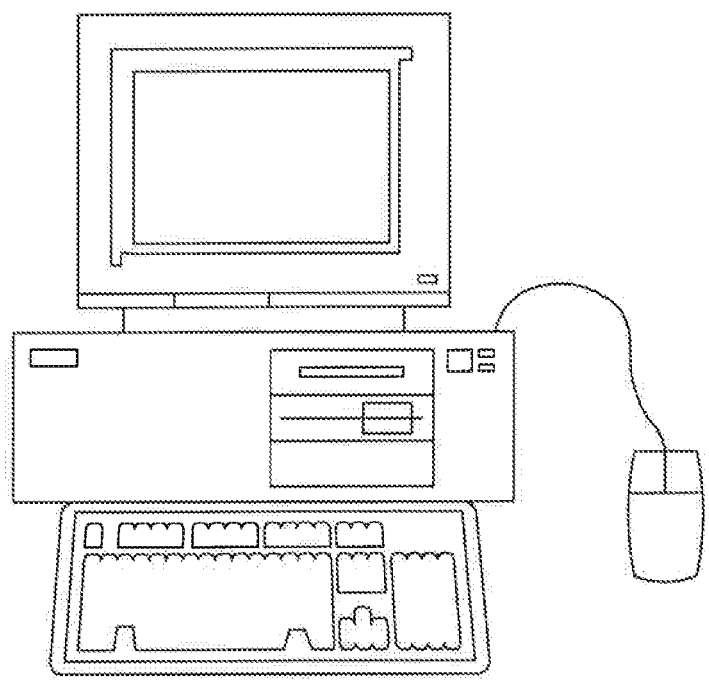
FIG. 21 illustrates a more detailed diagram of an exemplary client or server computer that can be used in one embodiment of the present invention.

FIG. 21 shows an exemplary computer system that can be utilized with the wearable devices 10. In an embodiment, a user interfaces with system 32 using a patient monitoring device 10 and then through a computer workstation system, such as shown in FIG. 21, a mobile device, and the like.

The communication network 166 may be the Network systems, among other things. The network may be a wireless, a wired network (e.g., using copper), telephone network, packet network, an optical network (e.g., using optical fiber), or a wireless network, or any combination of these. For example, data and other information may be passed between the computer and components (or steps) of a system of the invention using a wireless network using a protocol such as Wi-Fi (IEEE standards 802.11, 802.11a, 802.11b, 802.11e, 802.11g, 802.11i, 802.11n, and 802.11ac, just to name a few examples), near field communication (NFC), radio-frequency identification (RFID), mobile or cellular wireless (e.g., 2G, 3G, 4G, 3GPP LTE, WiMAX, LTE, Flash-OFDM, HIPERMAN, iBurst, EDGE Evolution, UMTS, UMTS-TDD, IxRDD, and EV-DO). For example, signals from a computer may be transferred, at least in part, wirelessly to components or other computers.

Figure 22:
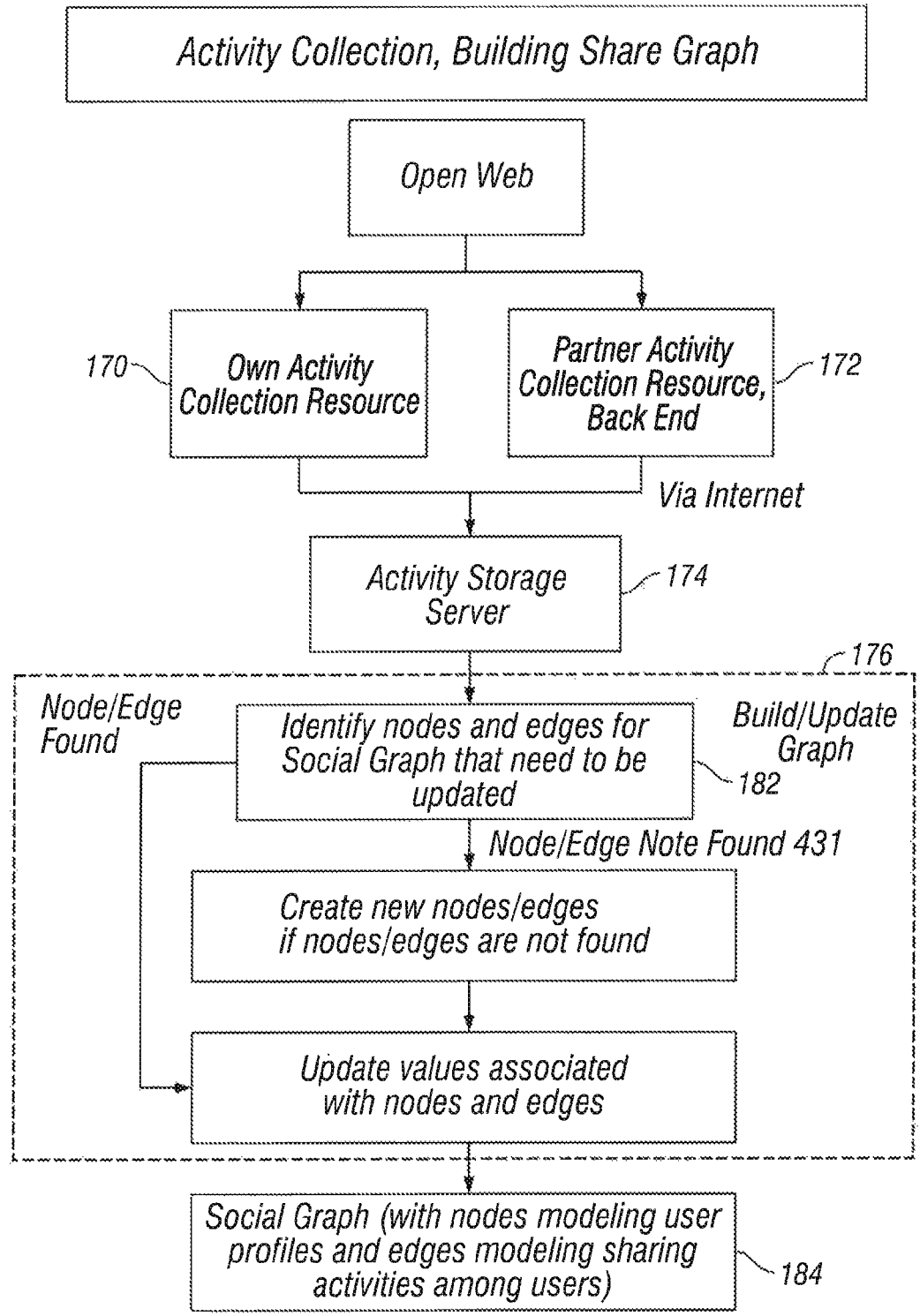
FIG. 22 illustrates a system for activity collection and building a social graph including sharing activity between users in one embodiment of the present invention.

FIG. 22 shows a system for activity collection and building a social graph for network patient monitoring device 10 users. The system monitors users as they surf the Web, their activities, locations, status, interests, and other things, This can be achieved without regard to whether the wearable device users 10 are logged into a membership site, such as a social networking site.

Resources 170 and 172 gather activity data and pass this data to an activity storage server 174, typically via Network Systems 108. Partner resource 172 may be processed by a partner back end, and then this data is passed to activity storage server 174.

Patient monitoring device 10 users can use social media sharing application or sites. Applications (e.g., a mobile device app or sites allow sharing of information with others. These can be used to collect activity data. A patient monitoring device 10 user (sender) can share information (e.g., video, photo, link, article, or other) by posting to a site. The patient monitoring device 10 user can post directly on the site or use an application program, such as a mobile application on a smartphone or tablet computer. When another user (recipient) clicks or vies the link, there is connection activity between the sender and recipient. This activity data is captured by system 32.

Messenger applications such as those on mobile device 74 or sites can allow Network Systems or Web messaging with others. Network Systems messaging is different from short messaging server (SMS) or text messaging. Messenger applications can be used to collect sharing activity data.

Users use messenger application to send links and other information to other users, and also achieve this using their wearable devices 10. A user (sender) can copy a link (e.g., via a clipboard) and send to one or more users via the messenger application with mobile device 74 and with its patient monitoring device 10. When a recipient user clicks on the link, there is connection activity between the sender and recipient for that link.

Sharing activity data can be captured as described above. There can be different data collectors for different devices and platforms. The activity data is transmitted to and stored at activity storage server 174, typically through Network Systems. Server 174 stores the data for further processing. There can be a significant amount of real-time data that is collected for processing. Distributed computing and processing can be used to process the data.

The activity data collected is stored at server 174, usually in a database or file systems on hard drives of server 174. There may be many terabytes of data that need are to be processed. Taking the stored activity data as input is a build-update graph component (e.g., executable code running on one or more servers or other computers). Build-update graph component 178 can run on the same server that stores the activity data, or may run on a separate server that accesses storage server 174.

In one embodiment, a build-update graph 180 builds or updates a social graph using the collected activity data. The social graph can be stored in one or more databases or file systems. In one embodiment, build-update graph 180 can include three components: (1) identify nodes and edges for social graph that need to be updated, (2) create new nodes/ edges if nodes/edges are not found, and (3) update values associated with nodes and edges.

For the incoming activity data collected, identify nodes 182 scan through and find the nodes and edges of the social graph that need to be updated.

When system 32 is processing a user activity data it has the ID of the patient monitoring device 10 user and attributes this activity to that patient monitoring device 10 user.

When a node or edge is found, update values update the node or an edge (e.g., associated with the node). When a node or edge is not found, a new node or edge is created in the graph. The result of build/update graph is a social graph 184 with nodes modeling user profiles and edge modeling sharing activities among users.

Figure 23:
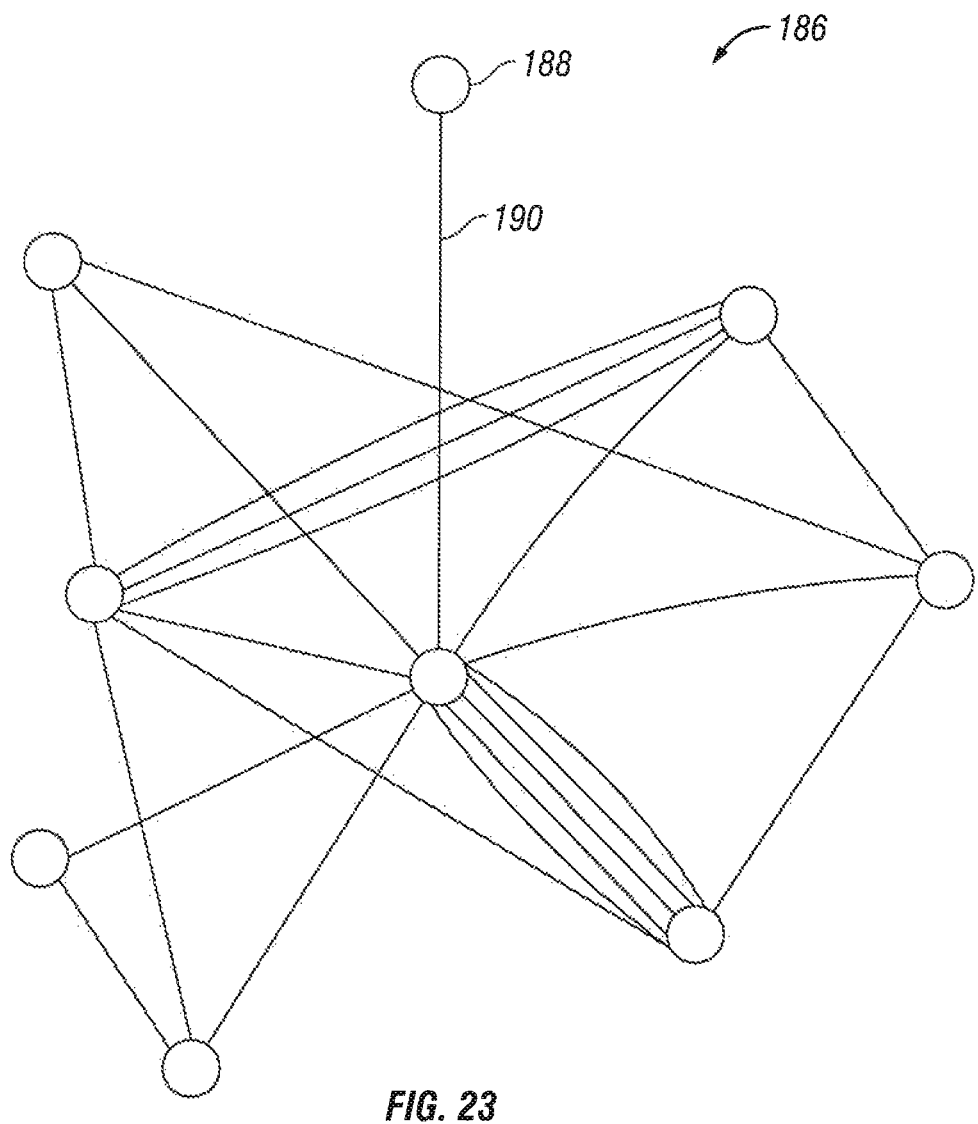
FIG. 23 illustrates a social graph with nodes representing users and edges representing sharing activity between the users in one embodiment of the present invention.

FIG. 23 shows a sample social graph 186 where circles 188 represent nodes and lines are edges 190 representing sharing interactions between nodes 182. There can be one or more edges 190 between two nodes 182. Several edges 190 between nodes 182 can indicate sharing activities along several categories: e.g., travel, computers, sports, and others.

Nodes 182 connected together directly have one degree of separation. Nodes 182 connected through one other node have two degrees of separation. Depending on a number of intervening nodes 182 between two nodes 182, this will be a number of degrees of separation between the two nodes 182.

In a specific implementation, edges 190 between nodes 182 indicate sharing activities along several categories such as travel, computers, sports, and the like. For each additional new sharing category, an additional edge 190 is added. In a specific implementation, for each additional new sharing interest category, an additional edge 190 is added. Further, in an implementation, the sharing interaction or edges 190 between the nodes 182 can be weighted (e.g., weighting in a range from 0 to 1), so that certain types of sharing interactions are given different significance. Weight can be used to represent a relative strength of interaction related to a particular interest category.

Some types of sharing activities that are tracked for the social graph (or share graph) include: sending messages between users; sending files between users; sending videos between users; sending an e-mail (e.g., Web e-mail) with a link from one user to another such as sharing a link to various social media sites; and sending instant messages between users. For mobile devices 74 the sharing activities can further include: sending SMS-type messages between users. In some embodiments, messages can be sending from wearable devices 10.

Once two users connect, such as one patient monitoring device 10 sending another patient monitoring device 10 user a message containing a link concerning a topic. When the recipient user clicks on the link from the sender user, system 32 will add an edge 190 to graph 186 to represent the activity. An edge 190 is added to the graph 186 to represent this sharing activity between the two users.

In a specific implementation, two patient monitoring device 10 users are connected when one user (sender) shares information with another user or group and the other user (recipient) consumes the information that was sent (e.g., clicked-back on the shared link, opened an attachment, opened a message). For example, simply placing a link on Facebook® wall so that all Facebook® "friends" can see this link or tweeting a link to Twitter® followers will not create a connection between the sender, or sharer, and people in the graph. This would create significant noise in the system. The connections are created between the sender and only those users who clicked back on (or otherwise consumed) the message.

In one embodiment, more recently sent messages are given a greater weight than older messages.

Figure 24:
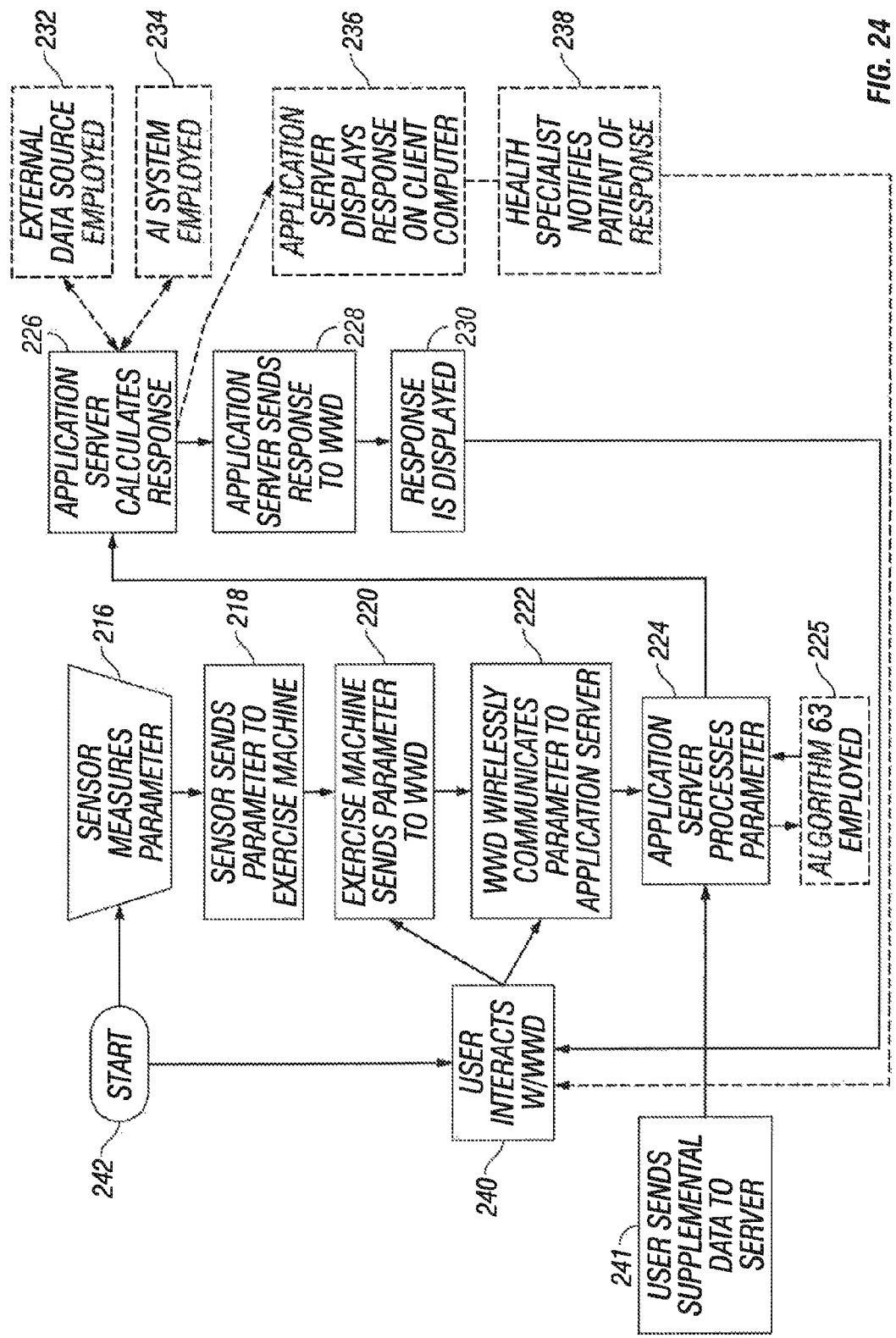
FIG. 24 illustrates an embodiment of the present invention directed to health management of a patient.

Referring to FIG. 24, the patient monitoring device 10 includes an application for monitoring exercise activity of a patient. The telemetry system 32 receiving exercise-related information directly or indirectly from the monitoring device 10 that indicates an amount or type of exercise performed by the patient. In one embodiment, the telemetry system 32 performs an analysis of the amount of exercise performed by the patient.

At least a portion of the amount of patient exercise or type of exercise analysis is communicated to the monitoring device.

In one embodiment, at least a portion of the analysis of the amount or type of patient exercise provides an indication of a physiologic status of the patient. The indication of the physiologic status of the patient can be received by the monitoring device 10 while the patient is exercising.

In one embodiment, the telemetry system 32 includes a database of a patient's health information. The patient's health information can include, one or more thresholds indicating an amount of exercise that should not be exceeded, one or more thresholds that the patient should be exceeded by the patient during exercise, and the like.

In various embodiments, the telemetry system 32 and/or the monitoring device 10 can be a mobile device. In one embodiment, the exercise is performed by the patient using an exercise device. In one embodiment, the exercise device includes one or more sensors that measure a patient physical parameter. In one embodiment, the exercise device communicates one or more signals to the monitoring device that is used for determining the amount or type of exercise. In one embodiment, the monitoring device 10 performs a conditioning of the one or more signals received from the exercise device. The telemetry system 32 can receive signals from the monitoring device that are conditioned. In one embodiment, the telemetry system 32 receives signals directly from the exercise device.

FIG. 24 illustrates one embodiment of a system for monitoring a patient's health, nutrition, exercise management and the like. As illustrated, the monitoring device 10 is in communication with an exercise machine used by a patient.

A program for monitoring the patient's health, nutrition, exercise and the starts at step 242 with a sensor measuring a health parameter (step 216), where the health parameter corresponds to health, fitness, nutrition, exercise, and the like. The sensor may send the parameter to the exercise machine (step 218).

The exercise machine then can then send the parameter to the patient monitoring device 10 (step 220). The patient monitoring device 10 wirelessly communicates the parameter to a telemetry system server or engine (step 222)

In another embodiment, entering the parameter is by user input (step 248). For example, the user may enter the parameter into the exercise machine or into the patient monitoring device 10. This parameter may correspond to an amount of exercise performed, an amount of food consumed, and the like.

Calculations by the telemetry engine or server may also take into account supplemental data sent by the user to the engine or server, e.g., in a wired fashion directly over the internet (step 241).

The application engine or server processes the parameter (step 224 and optionally step 225), and calculates a response (step 226) based at least in part on the parameter. The telemetry engine or server can optionally employ external data (step 232) or an AI system (step 234) in the calculation. The application engine or server then sends the response to the patient monitoring device 10 (step 228), where the response is displayed.

As an optional step, a health specialist may notify the patient of the response (step 238) after having the same displayed on their client computer (step 236). The health specialist may be replaced in this example by an application that may also include logic resources that perform analysis of signals from the exercise device and/or the monitoring device.

The foregoing description of various embodiments of the claimed subject matter has been provided for the purposes of illustration and description. It is not intended to be exhaustive or to limit the claimed subject matter to the precise forms disclosed. Many modifications and variations will be apparent to the practitioner skilled in the art. Particularly, while the concept "component" is used in the embodiments of the systems and methods described above, it will be evident that such concept can be interchangeably used with equivalent concepts such as, class, method, type, interface, module, object model, and other suitable concepts. Embodiments were chosen and described in order to best describe the principles of the invention and its practical application, thereby enabling others skilled in the relevant art to understand the claimed subject matter, the various embodiments and with various modifications that are suited to the particular use contemplated.

What is claimed is:

1. A system for using telemetry data based on a person monitoring, comprising:
   a person monitoring device that includes a microphone and sensors to determine air quality, sound level/quality, light quality and ambient temperature near the individual configured to assist to determine individual sleep information and sleep behavior information, the person monitoring device including an accelerometer or other movement detection device that measures movement of the person, the accelerator and the other movement detection device and the person monitoring device configured to calculate or derive sleep onset and wake time, sleep interruptions, and the quality and depth of sleep, a recording of one or more of the sensors being disabled by the monitoring device in response to location, acceleration, or lack of acceleration;
   ID circuitry at the monitoring device or the accelerometer or other movement detection device, and
   a telemetry system in communication with the monitoring device, the telemetry system including a database of ID's, the telemetry system in communication, the telemetry analyzing telemetry data received from the monitoring device based on sleep onset and wake time, sleep interruptions, and the quality and depth of sleep- and creating personalized information about the person.

2. The system of claim 1, wherein the telemetry system performs an analysis of the amount of the sleep onset and wake time, sleep interruptions, and the quality and depth of sleep of the person.

3. The system of claim 2, wherein at least a portion of the analysis of the amount of sleep onset and wake time, sleep interruptions, and the quality and depth of sleep of the person is communicated to the person.

4. The system of claim 2, wherein at least a portion of the analysis of the sleep onset and wake time, sleep interruptions, and the quality and depth of sleep of the person a status of the patient.

5. The system of claim 1, wherein the telemetry system includes a database of the person's sleep information.

6. The system of claim 1, wherein the telemetry system is a mobile device.

7. The system of claim 1, wherein the monitoring device is a mobile device.

8. The system of claim 1, wherein the telemetry system receives signals from the monitoring device that are conditioned.

9. A method for remotely determining sleep information about a person, comprising:
   using a monitoring device that includes a microphone and sensors to determine air quality, sound level/quality, light quality and ambient temperature near the individual configured to assist to determine individual sleep information and sleep behavior information, the monitoring including
   an accelerometer or other movement detection device that measures movement of the individual, a recording one or more sensors being disabled in response to location, acceleration, or lack of acceleration;
   using the monitoring device to assist in determining sleep onset and wake time, sleep interruptions, and the quality and depth of sleep of the person; and
   communicating via signals sleep information to a telemetry system that includes a database of patient ID's, and a database of patient information.

10. The method of claim 9, further comprising:
    creating conditioned signals from the monitoring device and the accelerometer or other movement device, with the conditioned signals being communicated wirelessly to the telemetry system.

11. The method of claim 9, further comprising:
    determining a status of the person in response to the signals.

12. The method of claim 9, further comprising:
    communicating at least a portion of the sleep onset and wake time, sleep interruptions, and the quality and depth of sleep to the person.

13. The method of claim 9, further comprising:
    communicating at least a portion of the sleep onset and wake time, sleep interruptions, and the quality and depth of sleep; to the person.

14. The method of claim 9, further comprising:
    accessing a database of a person's sleep onset and wake time, sleep interruptions, and the quality and depth of sleep; at the telemetry site.

15. The method of claim 9, wherein the telemetry system is a mobile device.

16. The method of claim 9, wherein the monitoring device is a mobile device.

17. The method of claim 9, further comprising:
    conditioning the one or more signals received from the monitoring device.

* * * * *